(12) United States Patent
Yoakim et al.

(10) Patent No.: US 7,273,861 B2
(45) Date of Patent: Sep. 25, 2007

(54) NON-NUCLEOSIDE REVERSE TRANSCRIPTASE INHIBITORS

(75) Inventors: Christiane Yoakim, Laval (CA); Jeffrey O'Meara, Boisbriand (CA); Bruno Simoneau, Laval (CA); William Ogilvie, Ottawa (CA); Robert Déziel, Ville Mont-Royal (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 176 days.

(21) Appl. No.: 10/662,606

(22) Filed: Sep. 15, 2003

(65) Prior Publication Data
US 2004/0132723 A1 Jul. 8, 2004

Related U.S. Application Data

(60) Provisional application No. 60/411,745, filed on Sep. 19, 2002.

(51) Int. Cl.
*A61P 31/18* (2006.01)
*A61K 31/551* (2006.01)
*C07D 471/22* (2006.01)

(52) U.S. Cl. ...................... 514/219; 540/555
(58) Field of Classification Search ................ 514/219; 540/555
See application file for complete search history.

(56) References Cited

FOREIGN PATENT DOCUMENTS

| EP | 0767172 | 4/1997 |
|---|---|---|
| EP | 0791594 | 8/1997 |
| WO | WO 02/076982 | 10/2002 |
| WO | WO 03/011862 | 2/2003 |

OTHER PUBLICATIONS

Nicholas K. Terrett et al; Imidazo[2',3':6,5]Dipyrido[3,2-b:2',3'-e]—1,4-Diazepines: Non-Nucleoside HIV-1 Reverse Transcriptase Inhibitors with Greater Enzyme Affinity than Nevlrapine; Bioorganic & Medicinal Chemistry Letters vol. 2 No. 12 pp. 1745-1750 (1992); Pergamon Press.
International Search Report Reference #PCT/CA 03/01410, 2004.

*Primary Examiner*—Brenda Coleman
(74) *Attorney, Agent, or Firm*—Michael P. Morris; Mary-Ellen M. Devlin; Alan R. Stempel

(57) ABSTRACT

Compounds represented by formula 1:

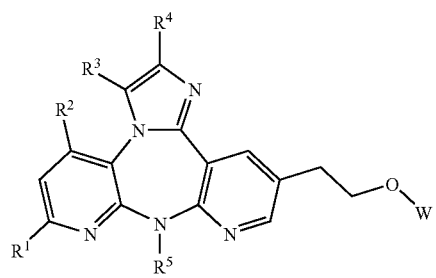

(1)

wherein $R^1$ is H, halogen, $(C_{1-4})$alkyl, $O(C_{1-4})$alkyl, and haloalkyl; $R^2$ is H or methyl; $R^3$ is H or $(C_{1-4})$alkyl; $R^4$ is H or $(C_{1-4})$alkyl; $R^5$ is $(C_{1-4})$alkyl, $(C_{1-4})$alkyl$(C_{3-7})$cycloalkyl or $(C_{3-7})$cycloalkyl; and W is a fused phenyl-5 or 6-membered heterocycle having one or two heteroatoms selected from N or S; or W is phenyl, 1,1'-biphenyl, 2,3-dihydro-1H-indene, 1,2,3,4-tetrahydronaphthyl, or naphthyl; said W being optionally substituted with $(C_{1-4})$alkyl, which in turn can be optionally substituted with a carboxy or $(C_{1-4})$alkoxycarbonyl, or a salt or ester thereof. The compounds have inhibitory activity against Wild Type, single and double mutant strains of HIV.

14 Claims, No Drawings

NON-NUCLEOSIDE REVERSE TRANSCRIPTASE INHIBITORS

CROSS-REFERENCE TO RELATED APPLICATIONS

Benefit of provisional application Ser. No. 60/411,745, filed Sep. 19, 2002 is hereby claimed.

TECHNICAL FIELD OF THE INVENTION

The invention relates to novel compounds and pharmaceutically acceptable salts thereof, their use, either alone or in combination with other therapeutic agents, in the treatment or prophylaxis of HIV infection, and to pharmaceutical compositions comprising these compounds that are active against NNRTI resistant mutants.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy from the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz, Abacavir, and Tenofovir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized, and resistance to known therapeutic agents is believed to be due to mutations in the RT gene. One of the more commonly observed mutants clinically for the non-nucleoside reverse transcriptase inhibitors, is the Y181C mutant, in which a tyrosine (Y), at codon 181, has been mutated to a cysteine (C) residue. Other mutants, which emerge with increasing frequency during treatment using known NNRTI antivirals, include single mutants K103N, V106A, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Compounds having tricyclic structures, which are inhibitors of HIV-1, are described in U.S. Pat. No. 5,366,972. Other inhibitors of HIV-1 reverse transcriptase are described in Hargrave et al., J. Med Chem., 34, 2231 (1991), Cywin et al., J. Med. Chem., 41, 2972 (1998) and Klunder et al., J. Med. Chem., 41, 2960 (1998).

U.S. Pat. No. 5,705,499 proposes 8-arylalkyl- and 8-arylheteroalkyl-5,11-dihydro-6H-dipyrido[3,2-b:2',3'-e][1,4]diazepines as inhibitors of RT. The exemplified compounds are shown to have some activity against HIV WT reverse transcriptase.

WO 01/96338A1, equivalent to U.S. Pat. No. 6,420,359 B1, discloses diazepine structures having quinoline and quinoline-N-oxide substituents as inhibitors of RT. The exemplified compounds have activity against HIV WT, single and double mutant strains.

U.S. Pat. No. 5,747,488 discloses 2-aryl-5,11-dihydro-6H-dipyrido[3,2-b:2',3'-e][1,4]-diazepines for treating HIV infection; and EP 791594 A2 discloses a related group of dipyridodiazepines for treating the same disease.

Terret et al., Biorg. Med. Chem. Lett., 2 (12), 1745 (1992) describe imidazo[2', 3':6, 5]-dipyrido[3,2-b:2',3'-e][1,4]diazepines as RT inhibitors.

WO 02/076982 and WO 03/011862 also disclose other diazepine-based HIV inhibitors.

SUMMARY OF THE INVENTION

The invention provides novel fused ring-containing compounds that are potent inhibitors of wild-type (WT) and double mutant strains of HIV-1 RT, particularly the double mutation K103N/Y181C.

In a first aspect the invention provides a compound represented by formula 1:

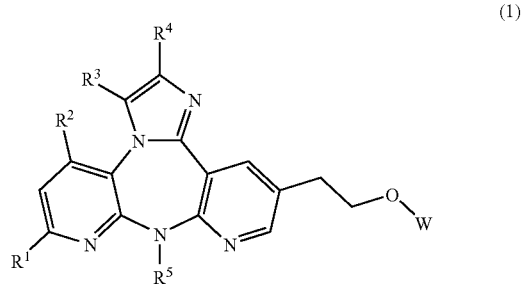

wherein
R¹ is selected from the group consisting of H, halogen, $(C_{1-4})$alkyl, $O(C_{1-4})$alkyl, and haloalkyl;
R² is H or Me;
R³ is H or $(C_{1-4})$alkyl;
R⁴ is H or $(C_{1-4})$alkyl;
R⁵ is $(C_{1-4})$alkyl, $(C_{1-4})$alkyl$(C_{3-7})$cycloalkyl, or $(C_{3-7})$cycloalkyl; and W is selected from:

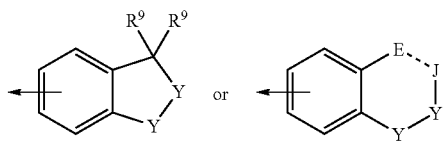 or 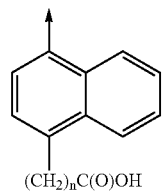

wherein,
a) one of Y is $SO_2$ and the other Y is $NR^6$, provided that both are not the same, wherein $R^6$ is selected from the group consisting of: H, $C(O)O(C_{1-4})$alkyl, $(C_{1-4})$ alkyl or $(C_{1-4})$ alkyl substituted with either a pyridinyl-N-oxide or $C(O)OR^8$ wherein $R^8$ is H or $(C_{1-4})$ alkyl; and each $R^9$ is independently H or $(C_{1-4})$ alkyl; and
b) E is $CR^{10}R^{10}$ wherein each $R^{10}$ is independently H or $(C_{1-4})$ alkyl, J is $CH_2$ and the dotted line represents a single bond; or
c) E and J are both $CR^{11}$ wherein each $R^{11}$ is independently H or $(C_{1-4})$ alkyl and the dotted line represents a double bond; or W is selected from:

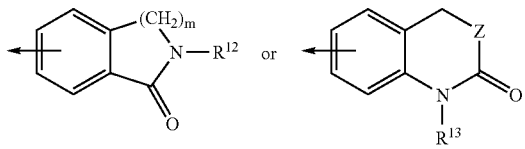

wherein,
m is 1 or 2,
$R^{12}$ is H or $(C_{1-4})$ alkyl,
$R^{13}$ is H or $(C_{1-4})$ alkyl, and
Z is O or Z is $NR^{14}$ wherein $R^{14}$ is H or $(C_{1-4})$ alkyl; or
W is selected from a group of aromatic radicals consisting of:

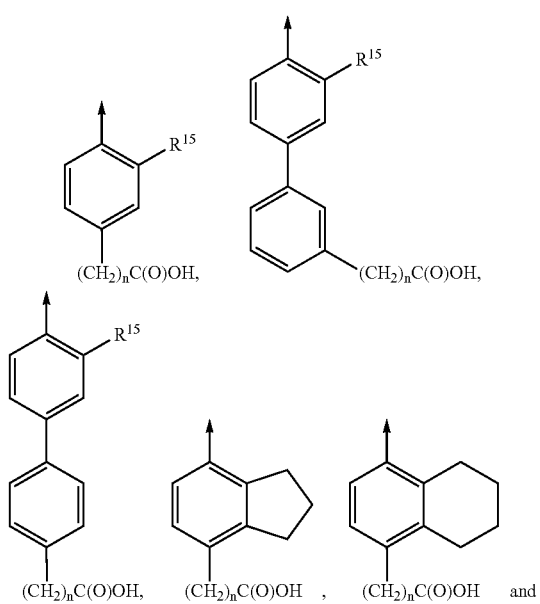

wherein $R^{15}$ is $(C_{1-4})$ alkyl or $CF_3$, and n is the integer 0, 1 or 2, or a pharmaceutically acceptable salt, ester or a prodrug thereof.

According to a second aspect of the invention, there is provided the use of a compound of formula 1, as described herein, for the manufacture of a medicament for the treatment or prevention of HIV infection.

According to a third aspect of the invention, there is provided the use of a compound of formula 1, as described herein, as an anti-HIV infective.

According to a fourth aspect of the invention, there is provided a pharmaceutical composition for the treatment or prevention of HIV infection, comprising a compound of formula 1, as described herein, or a pharmaceutically acceptable salt, ester or prodrug thereof, and a pharmaceutically acceptable carrier.

According to a fifth aspect of the invention, there is provided a method for the treatment or prevention of HIV infection, comprising administering to a patient an HIV inhibiting amount of a compound of formula 1 as described herein, or a pharmaceutically acceptable salt, ester or prodrug thereof.

According to a sixth aspect of the invention, there is provided a method for the treatment or prevention of HIV infection, comprising administering to a patient an HIV inhibiting amount of a pharmaceutical composition, as described herein.

According to a seventh aspect of the invention, there is provided a process for producing a compound of formula 1, comprising the step:

coupling a compound of formula 2:

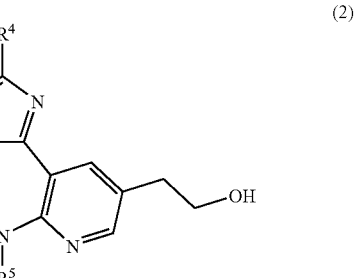

(2)

wherein $R^1$, $R^2$, $R^3$, $R^4$, and $R^5$ are as described herein, with a phenolic derivative selected from:

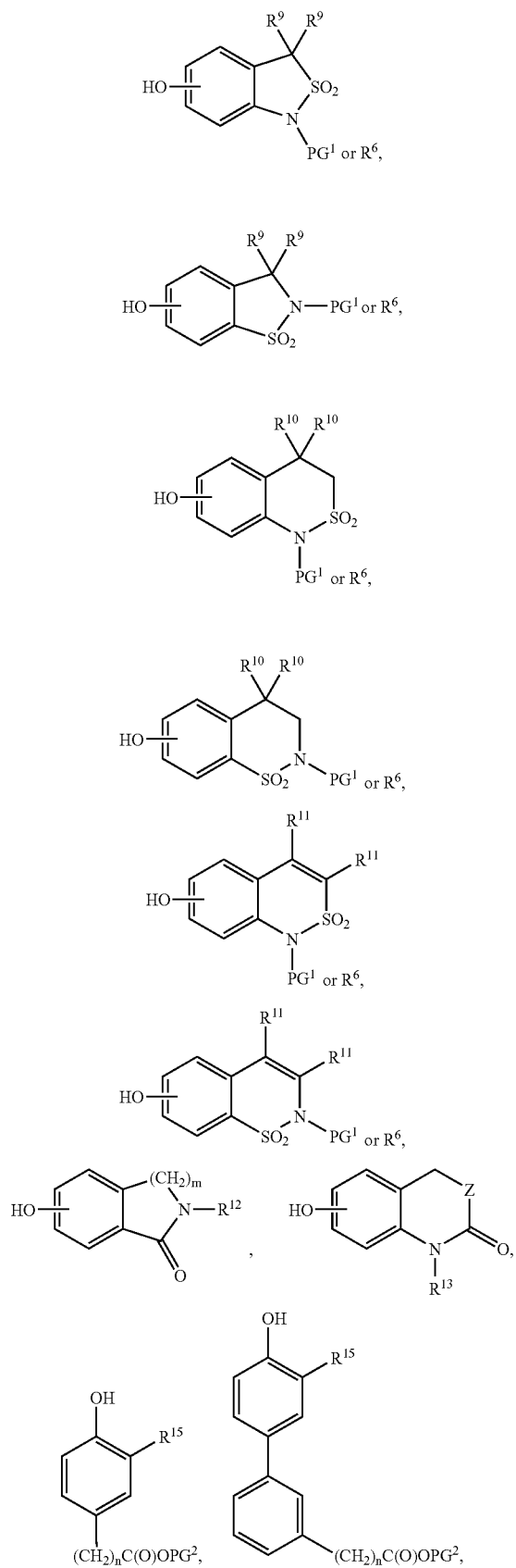

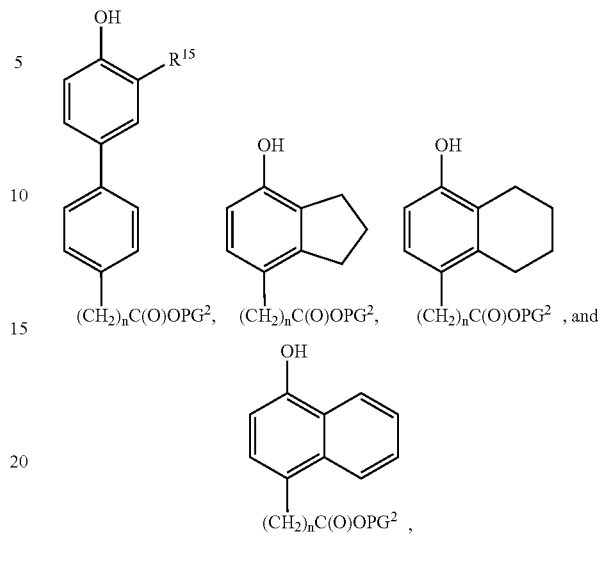

-continued

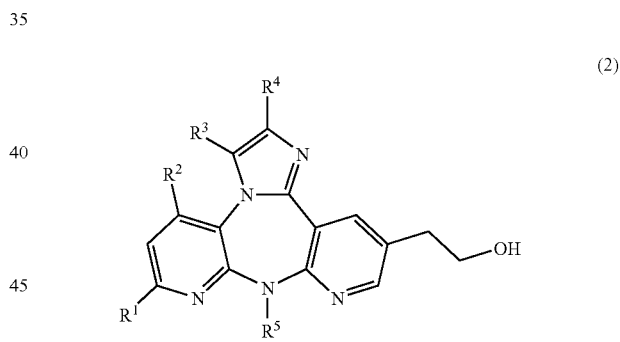

wherein $PG^1$ is a nitrogen protecting group and $PG^2$ is a carboxy protecting group, the protecting groups being removable under mildly acidic, mildly alkaline or reductive conditions, and $R^6$, $R^9$, $R^{10}$, $R^{11}$, $R^{12}$, $R^{13}$, $R^{14}$, $R^{15}$, m, n, and Z are as described herein.

According to an eighth aspect of the invention, there is provided an intermediate compound of formula 2:

(2)

wherein $R^1$, $R^2$, $R^3$, $R^4$, and $R^5$ are as described herein.

According to a ninth aspect of this invention, there is provided a pharmaceutical preparation for use in the treatment or prevention of HIV infection, wherein the active ingredient is a compound of formula 1 as defined herein, or a pharmaceutically acceptable salt, ester or prodrug thereof.

DETAILED DESCRIPTION OF THE INVENTION

Definitions

The following definitions apply unless otherwise noted:

As used herein, the term "carboxy protecting group" means a group capable of protecting a carboxy against undesirable reactions during synthetic procedures (see "Protective Groups in Organic Synthesis", Theodora W. Greene and Peter G. M. Wuts, third edition, 1999). For example, carboxy protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "$(C_{1-4})$alkyl", either alone or in combination with another radical, is intended to mean acyclic straight or branched chain alkyl radicals containing from one to four carbon atoms respectively. Examples of such radicals include methyl, ethyl, propyl, isopropyl, butyl, sec-butyl, and tert-butyl.

As used herein, the term "$(C_{3-7})$cycloalkyl" is intended to mean saturated cyclic hydrocarbon radicals containing from three to seven carbon atoms and includes cyclopropyl, cyclobutyl, cyclopentyl, cyclohexyl, and cycloheptyl.

The term "haloalkyl" as used herein, either alone or in combination with another substituent, means acyclic, straight or branched chain alkyl substituents as defined above having one or more hydrogens substituted for a halogen selected from bromo, chloro, fluoro or iodo.

The term "$\{(C_{1-6})alkyl-(C_{3-7})cycloalkyl\}$" as used herein means a cycloalkyl radical containing from 3 to 7 carbon atoms directly linked to an alkylene radical containing 1 to 6 carbon atoms; for example, cyclopropylmethyl, cyclopentylethyl, cyclohexylmethyl, and cyclohexylethyl.

As used herein, the term "inhibitor of HIV replication" means that the ability of HIV-1 reverse transcriptase to replicate a DNA copy from an RNA template is substantially reduced or essentially eliminated.

The terms "nitrogen protecting group" or "N-protecting group" as used herein interchangeably, means a group capable of protecting a nitrogen atom against undesirable reactions during synthetic procedures (see "Protective Groups in Organic Synthesis", Theodora W. Greene and Peter G. M. Wuts, third edition, 1999). For example, N-protecting include: Alkyl carbamates (such as methyl, ethyl or t-butyl) and aryl carbamates (such as benzyl).

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1-19, incorporated herein by reference).

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

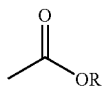

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

As used herein, the term "prevention" means the administration of a compound or composition according to the present invention post-exposure of the individual to the virus but before the appearance of symptoms of the disease, and/or prior to the detection of the virus in the blood.

As used herein, the term "prodrug" refers to pharmacologically acceptable derivatives, such that the resulting biotransformation product of the derivative is the active drug, as defined in compounds of formula 1. Examples of such derivatives include, but are not limited to, esters and amides. (see Goodman and Gilman in The Pharmacological Basis of Therapeutics, 9$^{th}$ ed., McGraw-Hill, Int. Ed. 1995, "Biotransformation of Drugs, p 11-16, incorporated herein by reference). Other suitable prodrug esters are found in Design of prodrugs, Bundgaard, H. Ed. Elsevier (1985) incorporated herewith by reference. Such pharmaceutically acceptable esters are usually hydrolyzed in vivo when injected in a mammal and transformed into the acid form of the compound of formula 1.

As used herein, the term "single or double mutant strains" means that either one or two amino acid residues that are present in WT HIV-1 strain have been replaced by residues not found in the WT strain. For example, the single mutant Y181 C is prepared by site-directed mutagenesis in which the tyrosine at residue 181 has been replaced by a cysteine residue. Similarly, for the double mutant K103N/Y181 C, an asparagine residue has replaced the lysine at residue 103 and a cysteine residue has replaced the tyrosine at residue 181.

Preferred Embodiments

Preferably, compounds of formula 1 as defined above, wherein, $R^1$ is selected from the group consisting of H, Cl, F, $(C_{1-4})$ alkyl and $CF_3$. More preferably, $R^1$ is H, Cl, F and Me.

Preferably, $R^2$, $R^3$ and $R^4$ is each independently H or Me.

Preferably, $R^5$ is ethyl or cyclopropyl.

Preferably, W is

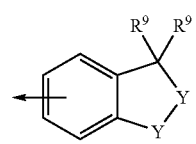

wherein Y is $SO_2$ and the other Y is $NR^6$, provided that both are not the same, $R^6$ is H, C(O)OMe, C(O)OEt, (4-pyridinyl-N-oxide)methyl, $CH_2C(O)OH$, $CH_2C(O)OMe$, $CH_2C(O)OEt$ or $CH_2C(O)OCMe_3$, and each $R^9$ is independently H or Me.

Preferably, W is

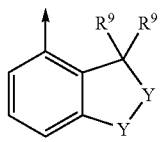

wherein Y is SO$_2$ and the other Y is NR$^6$, provided that both are not the same, R$^6$ is H, C(O)OEt, (4-pyridinyl-N-oxide)methyl, CH$_2$C(O)OH, CH$_2$C(O)OMe, CH$_2$C(O)OEt or CH$_2$C(O)OCMe$_3$, and each R$^9$ is independently H or Me. More preferably, R$^6$ is H, C(O)OEt or (4-pyridinyl-N-oxide)methyl. Most preferably, R$^6$ is (4-pyridinyl-N-oxide)methyl.

Preferably, W is

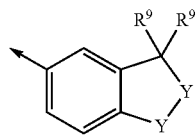

wherein Y is SO$_2$ and the other Y is NR$^6$, provided that both are not the same, R$^6$ is H, C(O)OEt, CH$_2$C(O)OH, CH$_2$C(O)OCMe$_3$, and each R$^9$ is independently H or Me. More preferably, R$^6$ is H and each R$^9$ is Me.

Preferably, W is

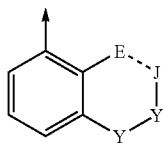

wherein E is CR$^{10}$R$^{10}$ wherein each of R$^{10}$ is independently H or Me, J is CH$_2$ and the dotted line represents a single bond; or E and J are both CR$^{11}$ wherein R$^{11}$ is H or Me and the dotted line represents a double bond; Y is SO$_2$ and the other Y is NR$^6$ wherein R$^6$ is hydrogen or methyl. Most preferably, W is

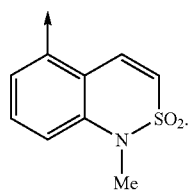

Preferably, W is

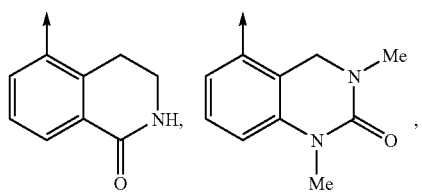

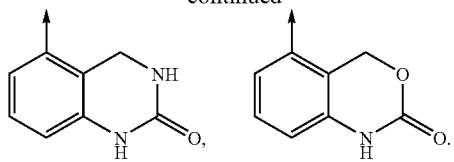

Preferably, R$^2$ is H or Me and W is

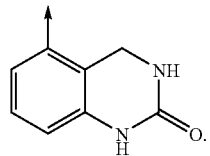

Preferably, W is selected from:

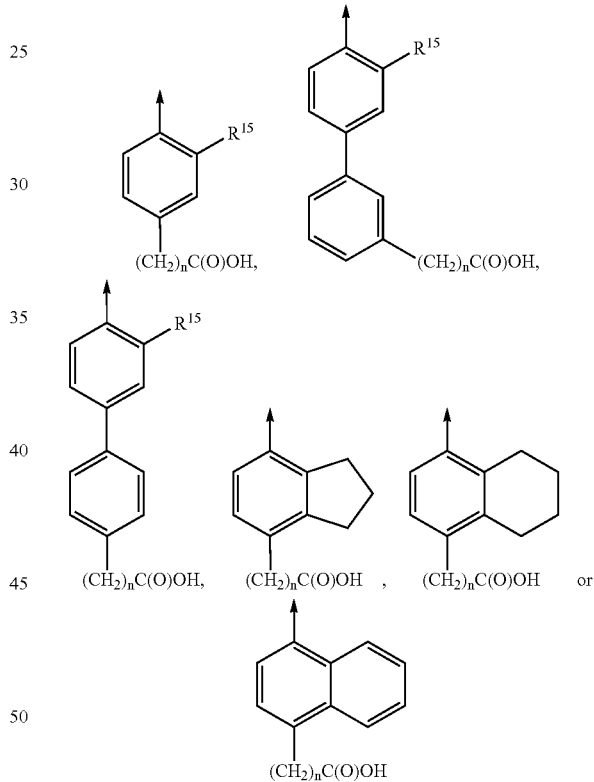

wherein R$^{15}$ is Me or Et, and n is 0 or 1. Most preferably, R$^{15}$ is Me.

Most preferably, W is

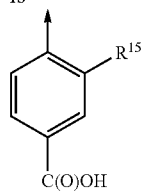

wherein R$^{15}$ is Me; or

W is

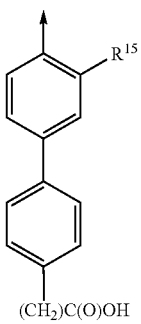

wherein $R^{15}$ is Me; or
W is

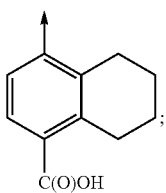

or W is

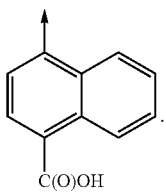

Still more preferably, $R^3$ is Me and W is

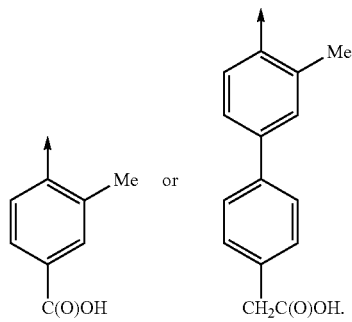

Specific Embodiments

Included within the scope of this invention is each single compound of Formula 1 as presented in Table 1.

Antiviral Activity

The compounds of formula 1 are effective inhibitors of wild type HIV as well as inhibiting the double mutation enzyme K103N/Y181C. The compounds of the invention may also inhibit the single mutation enzymes V106A, Y188L, K103N, Y181C, P236L and G190A. The compounds may also inhibit other double mutation enzymes including K103N/P225H, K103N/V1081 and K103N/L1001.

The compounds of formula 1 possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula 1, as described above. Whether it is termed treatment or prophylaxis, the compounds may also be used to prevent perinatal transmission of HIV-1 from mother to baby, by administration to the mother before giving birth.

The compounds of formula 1 may be administered in single or divided doses by the oral, parenteral or topical routes. A suitable oral dosage for a compound of formula 1 would be in the range of about 0.5 mg to 3 g per day. A preferred oral dosage for a compound of formula 1 would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula 1, include but are not limited to, nucleoside/nucleotide reverse transcriptase inhibitors (such as AZT and Tenofovir), non-nucleoside reverse transcriptase inhibitors (such as Nevirapine), protease inhibitors (such as Ritonavir), viral fusion inhibitors (such as T-20), CCR5 antagonists (such as SCH-351125), CXCR4 antagonists (such as AMD-3100), integrase inhibitors (such as L-870,810), TAT inhibitors, other investigational drugs (such as PRO-542, BMS-806, TMC-114 or Al-183), antifungal or antibacterial agents (such as fluconazole), and immunomodulating agents (such as Levamisole). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula 1 can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

Exemplary reaction schemes, disclosed in WO 01/96338A1, the contents of which are incorporated herein by reference, show the many synthetic routes to the tricyclic compounds [1(i), 1(ii) and 1(iii)], illustrated hereinafter. The compounds of the present invention may be made using the skills of a synthetic organic chemist. Exemplary reaction schemes are illustrated in Schemes 1 and 2. Substituents $R^1$, $R^2$, $R^3$, $R^4$, $R^5$ and W are as defined herein.

Scheme 1:

Synthesis of 9H-imidazo[1,2-d]dipyrido[2,3-b:3',2'-f][1,4]diazepine core

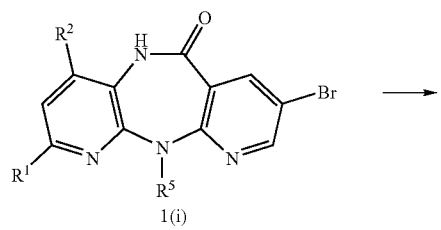

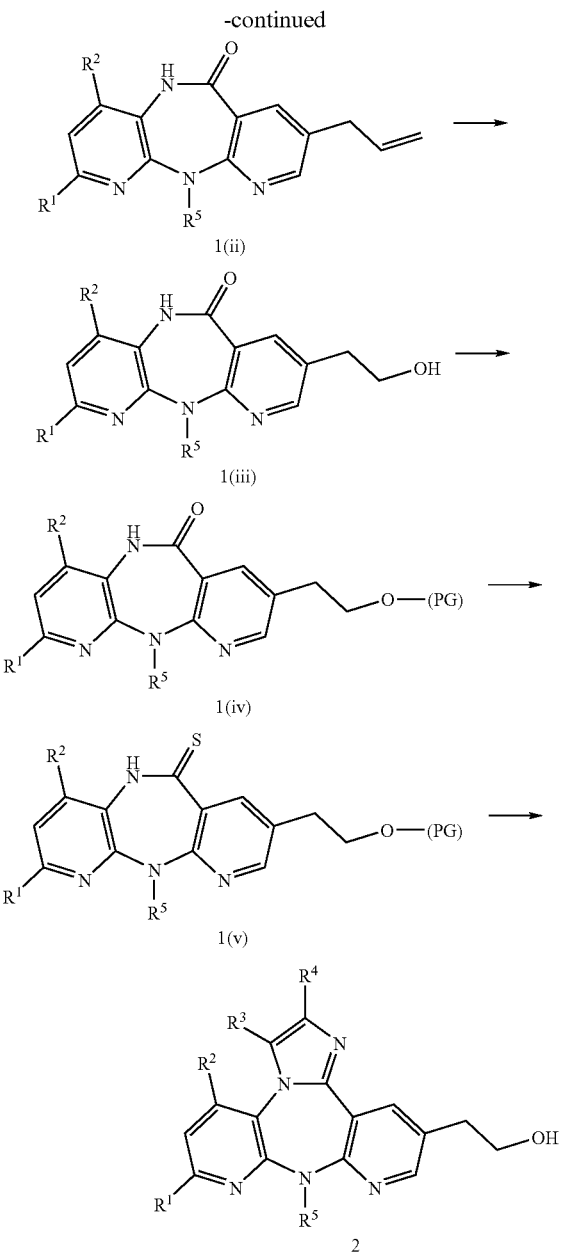

[(PG) represents a primary hydroxy protecting group]

Briefly, a 8-bromo-5,11-dihydro-6H-dipyrido[3,2-b:2',3'-e][1,4]diazepin-6-one derivative 1(i) can be converted into a 8-(2-propenyl) derivative 1(ii) using an allyl tin reagent (e.g. $CH_2=CHCH_2SnBu_3$) in the presence of a catalyst (e.g. $Pd(Ph_3)_4$). Cleavage of the terminal olefin in 1(ii) (e.g. ozonolysis followed by reduction) produces a 8-(2-hydroxyethyl) derivative 1(iii). Other methods for introducing the C-8 substituents are known to one skill in the art. Protection of the primary alcohol of derivative 1(iii) (see "Protective Groups in Organic Synthesis", Theodora W. Greene and Peter G. M. Wuts, second edition, 1991) gives amide 1(iv). The amides 1(iv) can be transformed to the corresponding thioamide 1(v) using, for example, the Lawesson's reagent.

The imidazole ring was elaborated from thioamide 1(v) using the methods described by Terret et al. (*Bioorg. Med. Chem. Lett*. 1992, 2, 1745) which simultaneously deprotects the primary alcohol to give 9H-imidazo[1,2-d]dipyrido[2,3-b:3',2'-f][1,4]diazepine compound of formula 2.

Scheme 2:

Introduction of W substituent

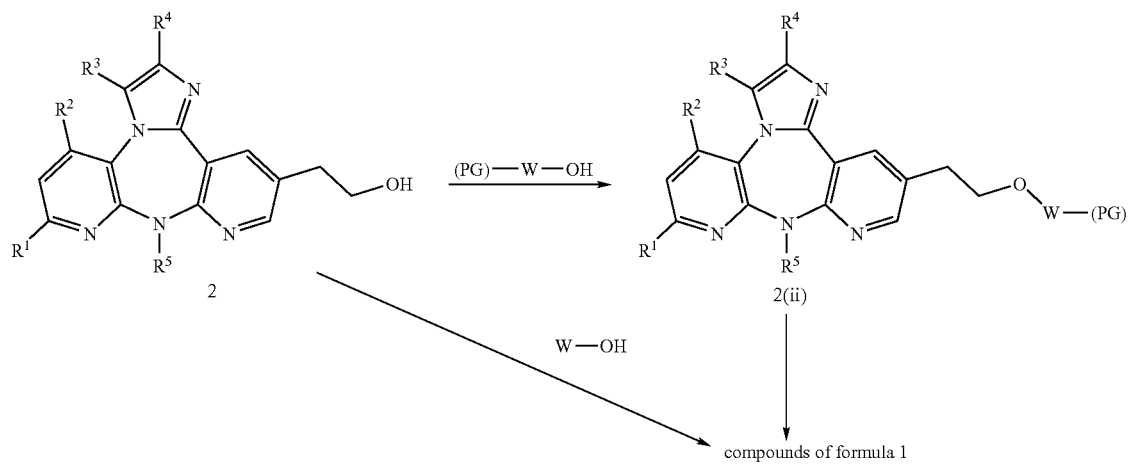

[(PG) represents a protective group]

Using a Mitsunobu-type coupling reaction, compound of formula 2 can be transformed into the corresponding compound of formula 1 via a coupling with an appropriate phenolic derivative. When the phenolic derivative does not require protection of an inherent secondary nitrogen, or carboxy group, the compound of formula 2 can be coupled with the appropriate phenolic derivative, i.e. W—OH, to provide the corresponding compound of formula 1. When the phenolic derivative does require protection of a nitrogen or carboxy group, the compound of formula 2 can be coupled with an appropriately protected intermediate of formula (PG)—W—OH to give a protected intermediate of formula. 2(ii). The protective group (PG) of intermediate 2(ii) can then be removed under suitable mildly acidic, mildly alkaline, or reductive condition to give the desired corresponding compound of formula 1. Other methods of condensation to produce the ether linkage in compounds of formula 1 are also contemplated, for example as $S_N2$ displacement of a suitably derivatized primary alcohol in 2 by W—OH or (PG)—W—OH.

The following reaction scheme wherein $R^1$ to $R^5$ inclusive are as described above, serves to illustrate alternative processes for preparing the compounds of formula 1:

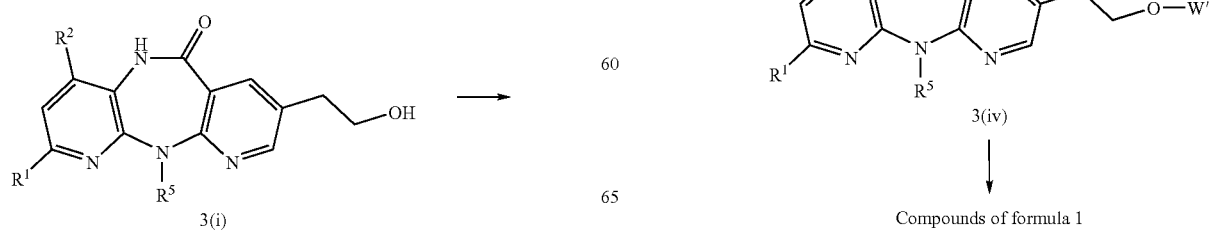

Compounds of formula 1

Briefly, using a Mitsunobu-type reaction, a 8-(2-hydroxyethyl) derivative 3(i), described in WO O1/96338A1, can be coupled with the appropriate phenolic derivative, described above (excluding the lactams of formula

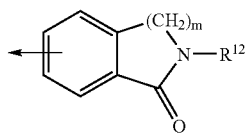

wherein m and $R^{12}$ are as defined hereinbefore) to obtain the corresponding diazepine-6-one derivative of formula 3(ii) wherein W' encompasses W as well as a protected W when required, c.f. $PG^1$ and $PG^2$ above. The derivative 3(ii) can be transformed into the corresponding thioamide 3(iii) using, for example, the Lawesson's reagent. Thereafter, the imidazole is elaborated from the thioamide using the methods described by Terret et al., Biorg. Med. Chem. Left., 2(12), 1745 (1992) to give diazepine intermediate 3(iv); or, in the instance where nitrogen or carboxy protection is not required to give directly a corresponding compound of formula 1. In the instance where nitrogen or carboxy protection is present, removal of the protecting group affords the desired corresponding compound of formula 1.

Still furthermore, the diazepine intermediate 3 (iv), related types thereof (e.g. wherein a carboxy is replaced by a carboxaldehyde), or certain compounds of formula 1, can serve as precursors for other compounds formula 1. Such precursors can be alkylated, esterified or functional groups thereof can be modified by well known transformations, e.g. a carboxaldehyde-containing precursor can be oxidized to a carboxy, to give corresponding compounds of formula 1.

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. Utilizing the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table 2 as $IC_{50}$ (nM) and $EC_{50}$ (nM).

EXAMPLES

The present invention is illustrated in further detail by the following non-limiting examples. All reactions were performed in a nitrogen or argon atmosphere unless otherwise stated. Temperatures are given in degrees Celsius. Solution percentages or ratios express a volume to volume relationship, unless stated otherwise.

Abbreviations or symbols used herein include: DEAD: diethyl azodicarboxylate; DIAD: diisopropyl azodicarboxylate; DIEA: diisopropylethylamine; $Et_2O$: diethyl ether; HPLC: high performance liquid chromatography; iPr: isopropyl; Me: methyl; MeOH: methanol; MeCN: acetonitrile; NBS: N-bromosuccinimide; Ph: phenyl; TBE: tris-borate-EDTA; TBTU: 2-(1H-benzotriazol-1-yl)-N,N,N',N'-tetramethyluronium tetrafluoroborate; TFA: trifluoroacetic acid; THF: tetrahydrofuran; PFU: plaque forming units; DEPC: diethyl pyrocarbonate; DTT: dithiothreitol; EDTA: ethylenediaminetetraacetate; UMP: uridine 5'-monophosphate; UTP: uridine 5'-triphosphate; MES: 2-(n-morpholino) ethanesulfonic acid; SDS-PAGE: sodium dodecyl sulfate-polyacrylamide gel electrophoresis; MWCO: molecular weight cut-off; Bis-Tris Propane: 1,3-Bis{tris(hydroxymethyl)-methylamino}propane; GSH: reduced glutathione; OBG: n-Octyl-β-D-glucoside; AlBN: 2,2'azobisisobutyronitrile.

Example 1

8-{2-{{(1,1-Dimethylethyl)dimethylsilyl}oxy}ethyl}-5,11-dihydro-9-ethyl-6H-dipyrido[3,2-b:2',3'-e][1,4]diazepin-6-thione

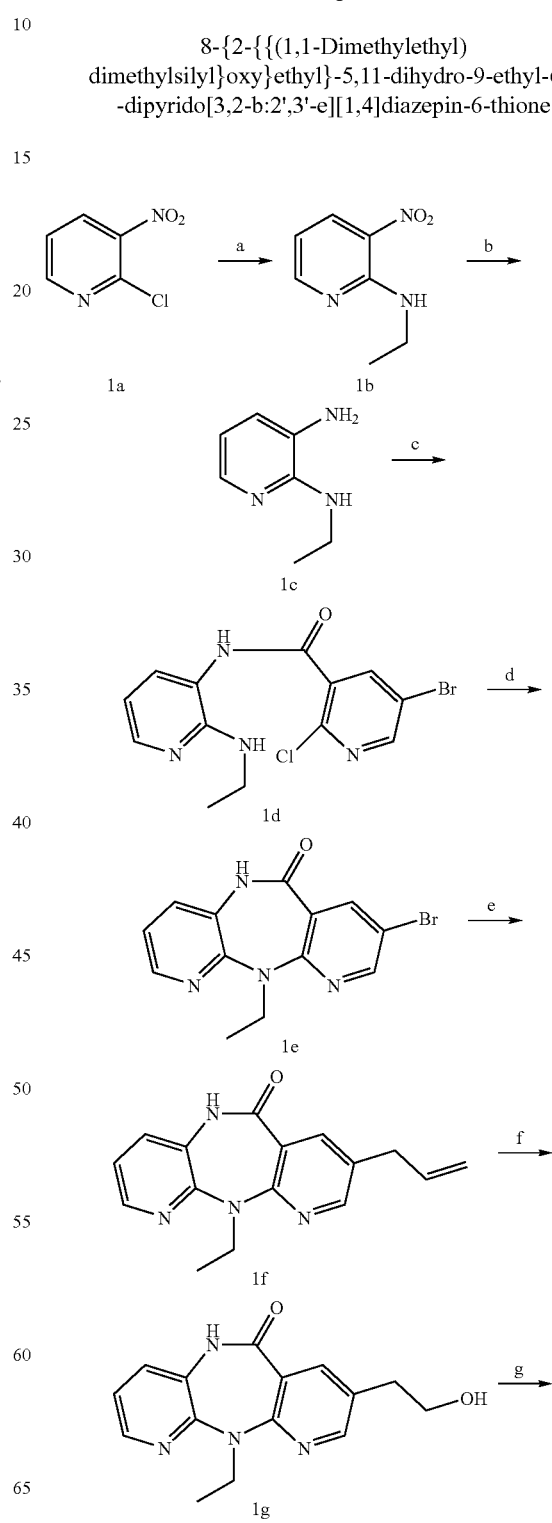

-continued

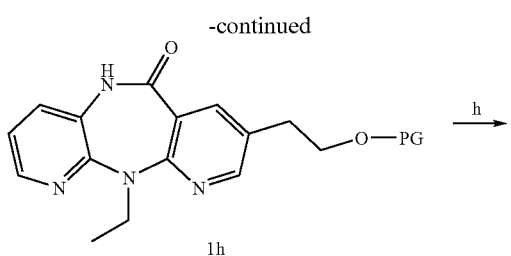

1h

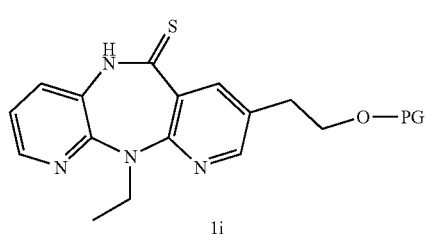

1i

PG = tert-butyldimethylsilyl

Step a:

To a solution of 2-chloro-3-nitropyridine 1a (51 g, 325 mmol) in THF (650 mL) was added a 2 M solution of ethylamine in THF (365 mL, 731 mmol). The reaction was stirred at room temperature overnight. The reaction mixture was poured into water (~1.5 L) and the resulting solid was filtered and dried under reduced pressure to give compound 1b (52 g).

Step b:

A solution of 2-(ethylamino)-3-nitropyridine 1b (52 g) in MeOH (600 mL) was stirred overnight at room temperature under hydrogen (1 atm.) in the presence of 20% Pd(OH)$_2$/C (10.4 g). The catalyst was removed by filtration through diatomaceous earth. The filtrate was concentrated under reduced pressure to give compound 1c as a black solid (39 g, 88% yield over the 2 steps).

Step c:

To a cooled solution of 3-amino-2-(ethylamino)pyridine 1c (30.6 g, 223 mmol) in MeCN (740 mL) was added solid NaHCO$_3$ (56.3 g, 669 mmol). After 5 min, crude 5-bromo-2-chloro-3-pyridinecarbonyl chloride (prepared from 5-bromo-2-hydroxy-3-pyridinecarboxylic acid and SOCl$_2$ [as described by T. W. Gero et al. in *Synth. Commun.* 1989, 19, 553-559 (incorporated herein by reference) but with omission of the aqueous work-up] was added (1 equiv., 223 mmol). After 2 h, the reaction mixture was poured over ice/water (1.5 L) and the resulting solid was filtered, rinsed with water and then hexane. After drying under reduced pressure overnight, compound 1d was obtained as a black solid (54.9 g, 69% yield).

Step d:

To a solution of 2-chloro-N-{2-(ethylamino)-3-pyridinyl}-5-bromo-3-pyridinecarboxamide 1d (54.9 g, 154.4 mmol) in pyridine (308 mL) at 50° C. was added dropwise a 1 M solution of NaHMDS (sodium hexamethyldisilazide) in THF (355 mL, 355 mmol). After 10 min, the reaction was allowed to cool to room temperature, and then was poured over ice water (2 L). The resulting solid was filtered, rinsed with water and then hexane. The solid was dried under reduced pressure to give compound 1e (36 g, 75% yield) as a dark green solid.

Step e:

Allyltributyltin (1.2 mL, 3.7 mmol) and Pd(Ph$_3$P)$_4$ (358 mg, 0.31 mmol) were added to a degassed (N$_2$ through solution for 30 min) solution of 1e (1.0 g, 3.1 mmol) in DMF (12 mL) at room temperature. The mixture was stirred at 90° C. for 1.5 h then was cooled to room temperature and concentrated under reduced pressure. The residue was purified by flash chromatography (hexane/EtOAc, 2/1) to give compound 1f (523 mg, 59% yield).

Step f:

A stream of ozonized oxygen was bubbled through a cold (−78° C.) solution of 1f (523 mg, 1.9 mmol) in CH$_2$Cl$_2$ (40 mL) and MeOH (40 mL) for 2.5 h. A stream of N$_2$ was next bubbled through the solution for 15 min and then solid NaBH$_4$ (138 mg, 3.7 mmol) was added to the solution. The reaction mixture was allowed to warm to room temperature. After 1 h, aqueous saturated NH$_4$Cl (20 mL) was added and the mixture was stirred at room temperature for 2 h. The organic solvents were removed under reduced pressure. Water (30 mL) and CHCl$_3$ (30 mL) were added to the residue. The phases were separated and the aqueous layer was extracted with CHCl$_3$ (3×10 mL). The combined organic layers were dried (MgSO$_4$), filtered and concentrated under reduced pressure. The residue was purified by flash chromatography (EtOAc) to give compound 1 g (501 mg, 94% yield) as a white solid.

Step g:

To a solution of 1 g (2.4 g, 8.5 mmol) in DMF (32 mL) was added imidazole (1.2 g, 17 mmol) and tert-butyldimethylsilyl chloride (1.6 g, 10.7 mmol). The reaction mixture was stirred at room temperature overnight. The mixture was diluted in EtOAc and washed successively with water, brine, dried (MgSO$_4$), filtered and concentrated under reduced pressure to give 1 h (3.1 g, 90% yield) as a white solid.

Step h:

A mixture of 1 h (3.1 g, 7.7 mmol) and Lawesson's reagent (3.3 g, 8.1 mmol) in THF (100 mL) was heated at 80° C. for 2 h. After cooling to room temperature, the reaction mixture was concentrated to dryness. The resulting residue was purified by flash chromatography (hexane/EtOAc, 3/1) to give compound 1i (2.1 g, 67% yield).

Example 2

(Entry 110) 9-Ethyl-3-methyl-12-{2-{(1,2,3,4-tetrahydro-1-oxo-5-isoquinolinyl)oxy}ethyl}-9H-imidazo[1,2-d]dipyrido[2,3-b:3',2'-f][1,4]diazepine

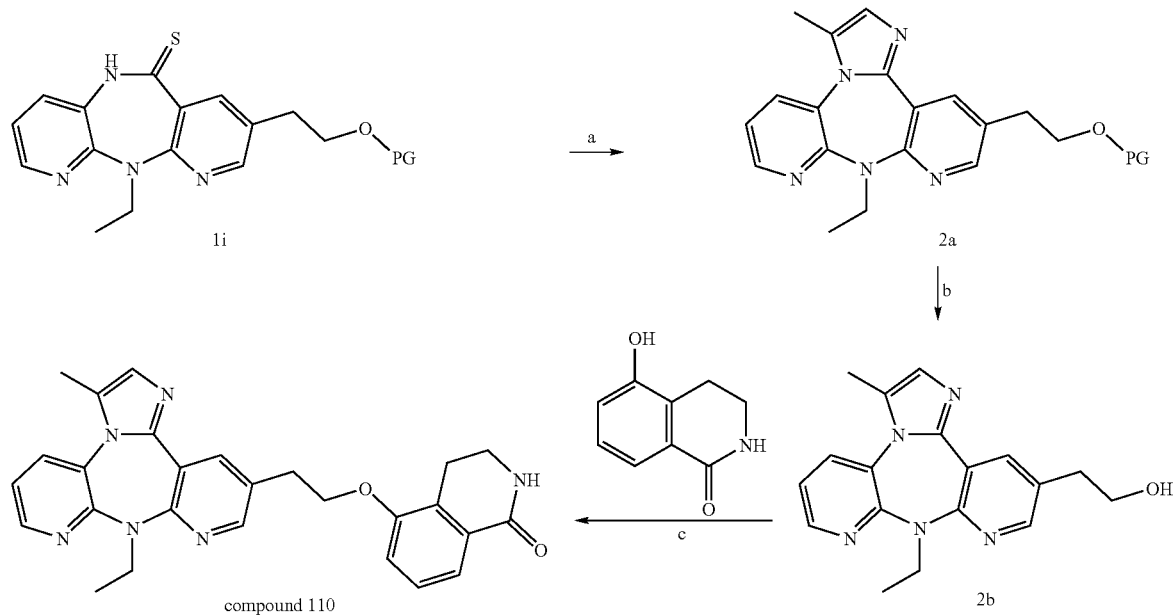

PG = tert-butyldimethylsilyl

Step a:

A mixture of thioamide 1i (5.6 g, 13.5 mmol) and propargylamine (21.5 g, 390 mmol) in n-butanol (100 mL) was heated at 100° C. for 2 h. The reaction mixture was concentrated under reduced pressure and the resulting residue was purified by flash chromatography (hexane/EtOAc, 2/1) to give compound 2a (4.9 g, 83% yield) as a yellow solid.

Step b:

To a solution of silyl ether 2a (4.9 g, 11.2 mmol) in THF (120 mL) was added a solution of 1.0 M tetrabutylammonium fluoride in THF (20.2 mL, 20.2 mmol). After 1 h at room temperature, the reaction mixture was evaporated to dryness and the resulting residue was purified by flash chromatography (EtOAc/EtOH, 10/1) to give compound 2b (3.3 g, 93% yield) as a yellow solid.

Step c:

A solution of DEAD (57 μL, 0.55 mmol) in THF (3 mL) was added dropwise to a solution of 2b (89 mg, 0.28 mmol), Ph₃P (145 mg, 0.55 mmol) and 5-hydroxy-3-4-dihydro-2H isoquinolin-1-one (45 mg, 0.28 mmol) in THF (10 mL) at room temperature. After 2 h, the reaction mixture was concentrated under reduced pressure and the resulting residue was purified by flash chromatography (EtOAc/EtOH, 95/5) to give compound 110 (36 mg, 28% yield) as a white solid.

Example 3

Entry (119) 4'-{(9H-imidazo[1,2-d]dipyrido[2,3-b:3',2'-f][1,4]diazepin-12-yl)ethoxy}-3'-methyl-[1,1'-biphenyl]4-acetic acid

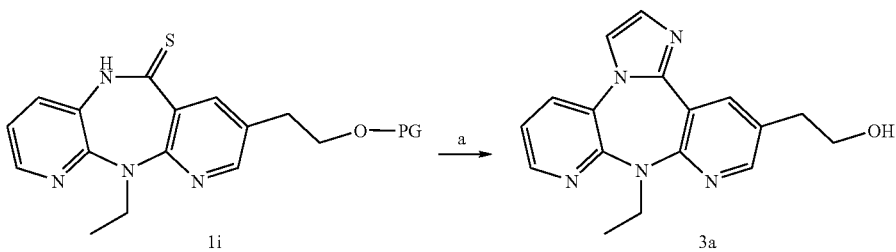

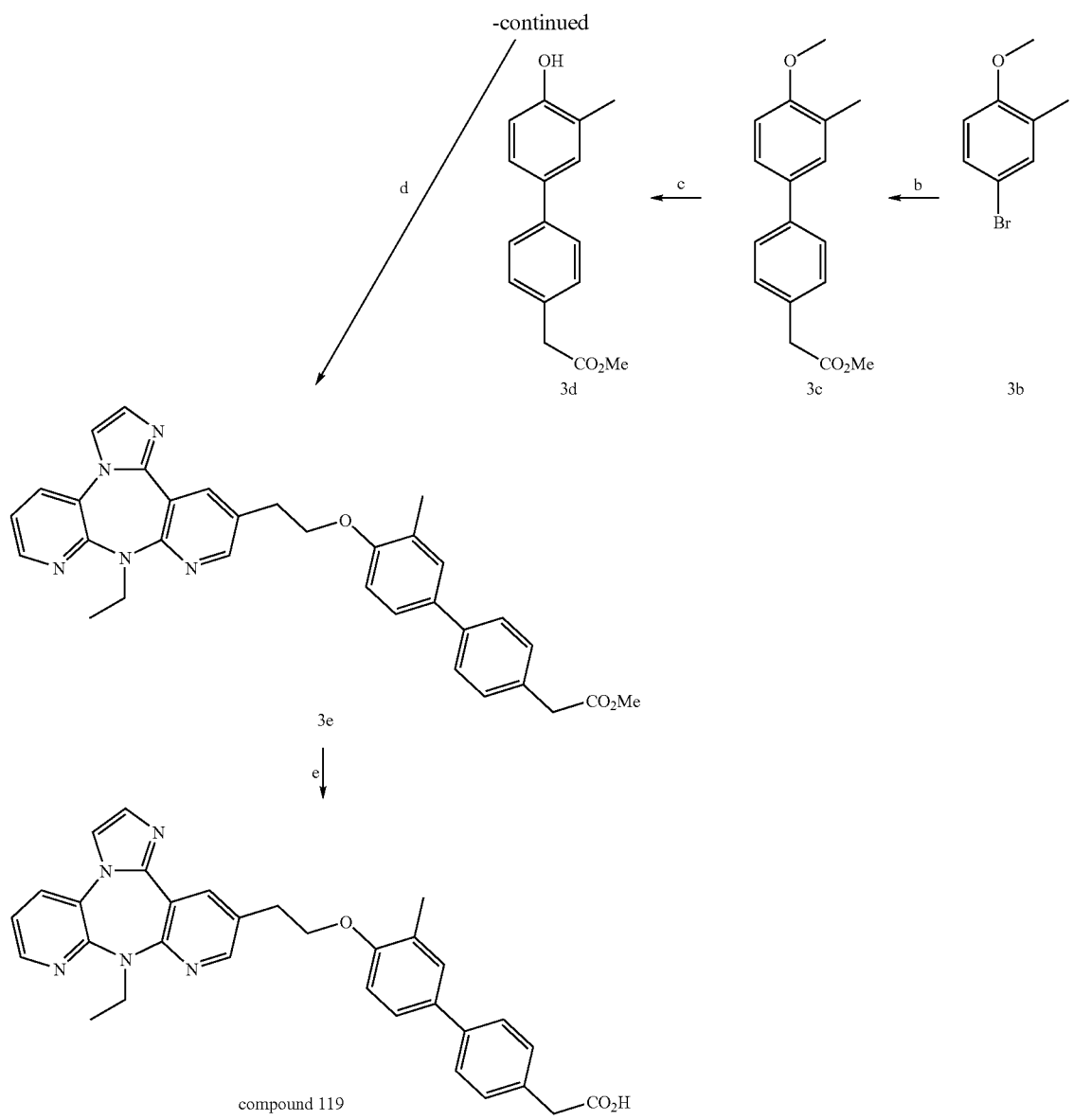

PG = tert-butyldimethylsilyl

Step a:

A mixture of thioamide 1i (2.1 g, 5.1 mmol) and aminoacetaldehyde dimethylacetal (9 mL, 90 mmol) in n-butanol (40 mL) was heated at 100° C. After 2 h, concentrated sulfuric acid (8 mL) was added and heating was continued for 1 h. The reaction mixture was cooled to room temperature and diluted with EtOAc. A saturated aqueous NaHCO$_3$ solution was added (pH-10). After phase separation, the aqueous phase was re-extracted with EtOAc. The combined organic phases were successively washed with water and brine, dried (MgSO$_4$), filtered and evaporated to dryness. The resulting residue was purified by flash chromatography (CH$_2$Cl$_2$/EtOAc, 1/3; followed by CHCl$_3$/EtOH, 10/1) to give compound 3a (770 mg, 50% yield) as a yellow solid.

Step b:

To a degassed (argon) solution of 3b (10.0 g, 49.7 mmol) in DMF (310 mL) was added bis(pinacolato)diborane (13.9 g, 54.7 mmol), KOAc (14.2 g, 149 mmol) and PdCl$_2$dppf (1:1 complex with CH$_2$Cl$_2$, 4.87 g, 5.96 mmol). The reaction mixture was heated to 80° C. for 24 h then was cooled to 25° C. 4-Bromobenzeneacetic acid (21.4 g, 99.5 mmol), aqueous 2 M Na$_2$CO$_3$ solution (124 mL, 248 mmol) and additional PdCl$_2$dppf (1:1 complex with CH$_2$Cl$_2$, 4.87 g, 5.96 mmol) were added to the mixture. The reaction mixture was heated to 80° C. for 12 h. The cooled mixture was acidified with aqueous 4 N HCl solution and extracted with EtOAc (3×). The combined organic layers were successively washed with water (2×) and brine, dried (MgSO$_4$), filtered and concentrated under reduced pressure. The crude resulting acid was dissolved in Et$_2$O and was treated with excess ethereal CH$_2$N$_2$ solution (ca. 0.6 M). The mixture was concentrated under reduced pressure. The residue was purified by flash chromatography (hexane/EtOAc, 19/1) to give 3c (4.25 g, 32% yield) as a pale yellow solid.

Step c:

A 1.0 M BBr$_3$ solution in CH$_2$Cl$_2$ (20.0 mL, 20.0 mmol) was added slowly to an ice-cold solution of 3c (2.60 g, 9.62 mmol) in CH$_2$Cl$_2$ (96 mL). The reaction mixture was stirred at 25° C. for 2 h then was cooled to 0° C. MeOH (5 mL) was slowly added, the mixture was poured into water and extracted with EtOAc (3×). The combined organic layers were washed with brine, dried (MgSO$_4$), filtered and concentrated under reduced pressure. The residue was purified by flash chromatography (hexane/EtOAc, 4/1) to give 3d (1.70 g, 70% yield) as a white solid.

Step d:

A solution of DIAD (77 μL, 0.39 mmol) in THF (0.8 mL) was added over 2 h to an ice-cold solution of 3a (99.9 mg, 0.32 mmol), 3d (100 mg, 0.39 mmol) and PPh$_3$ (102 mg, 0.39 mmol) in THF (3.3 mL). The reaction mixture was stirred at 25° C. for 16 h then was concentrated under reduced pressure. The residue was purified by flash chromatography (toluene/EtOAc, 3/2) to give 3 (54 mg, 30% yield).

Step e:

A solution of 3e (54.0 mg, 0.099 mmol) and aqueous 1 N NaOH solution (3.00 mL, 3.00 mmol) in THF (0.67 mL) and MeOH (0.33 mL) was stirred at 25° C. for 1 h. The reaction mixture was diluted with water and the resulting solution was washed with EtOAc (2×). The aqueous layer was acidified with aqueous 1 N HCl solution and extracted with EtOAc (3×). The combined organic layers were washed with brine, dried (MgSO$_4$), filtered and concentrated under reduced pressure. The resulting acid was dissolved in THF and treated with 1 equivalent of aqueous 0.02 N NaOH solution. The resulting solution was diluted with water then was frozen and lyophilized to give the sodium salt of compound 119 (44 mg, 80% yield) as a white solid.

Example 4

(Entry 101)

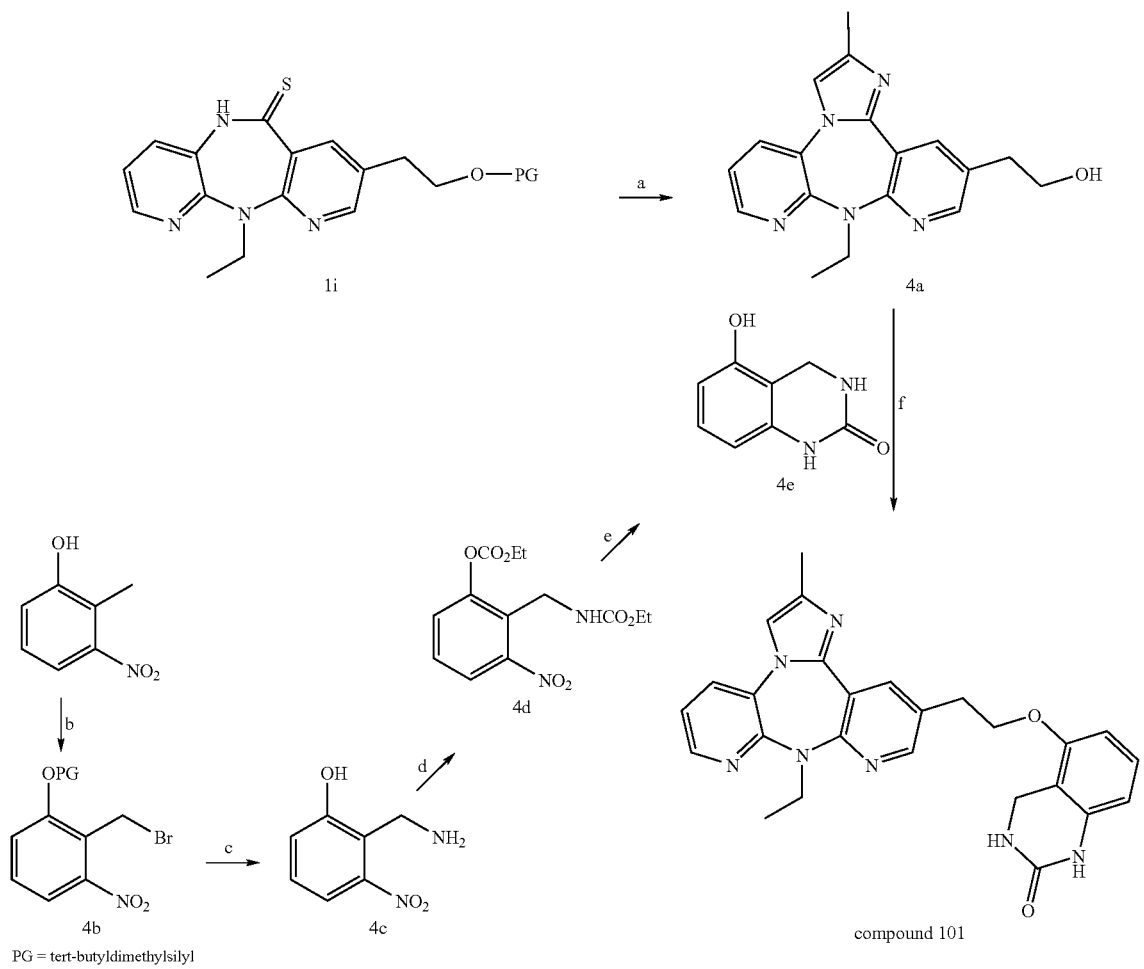

Step a:

A mixture of thioamide 1i (100 mg, 0.24 mmol) and 2-aminopropionaldehyde dimethylacetal (0.6 mL, 4.8 mmol) in n-butanol (3 mL) was heated at 110° C. for 2 days. Concentrated sulfuric acid (0.1 mL) was added and heating was continued for 1 h. The reaction mixture was cooled to room temperature and diluted with EtOAc. A saturated aqueous NaHCO₃ solution was added (pH~10). After phase separation, the aqueous phase was re-extracted with EtOAc. The combined organic phases were successively washed with water and brine, dried (MgSO₄), filtered and evaporated to dryness. The resulting residue was purified by flash chromatography (MeOH/EtOAc, gradient 2% to 5%) to give compound 4a (36 mg, 46% yield) as a clear gum.

Step b:

To a solution of 2-methyl-3-nitrophenol (10.0 g, 65.3 mmol) in THF (300 mL) were added imidazole (5.8 g, 85 mmol) and tert-butyldimethylsilyl chloride (10.8 g, 71.8 mmol). The reaction mixture was stirred at room temperature overnight. The mixture was diluted in EtOAc and washed successively with water and brine, dried (MgSO₄), filtered and concentrated under reduced pressure. The residue was filtered through a thin pad of silica gel (hexane/Et₂O). The resulting yellow oil (13.3 g) was dissolved in CCl₄, AIBN (350 mg) and NBS (10.2 g, 57.3 mmol) was added. The reaction mixture was irradiated using a sun lamp (275 W) for 3 h, diluted in Et₂O, filtered through a thin pad of silica gel, concentrated to dryness. The residue was purified by flash chromatography (hexane/EtOAc, 9/1) to give 4b (15 g, 66% yield over 2 steps).

Step c:

To a solution of 4b (8.0 g, 23.1 mmol) in THF (100 mL) was added a solution of NaN₃ (7.7 g, 118 mmol) in water (10 mL). After 2 h at room temperature, the reaction mixture was diluted with EtOAc and washed successively with water, brine, dried (MgSO₄), filtered and concentrated under reduced pressure. The resulting solid was dissolved in THF (100 mL) and water (1.5 mL) and triphenylphosphine (7.7 g, 29.3 mmol) were added. After 16 h at room temperature, the reaction mixture was diluted with EtOAc and washed successively with water, brine, dried (MgSO₄), filtered and concentrated under reduced pressure. The residue was purified by flash chromatography (EtOAc/MeOH, 9/1, then 8/2) to give 4c (2.6 g, 68% yield) as a yellow solid.

Step d:

To a solution of 4c (2.1 g, 12.5 mmol) in THF (150 mL) were added Et₃N (4.4 mL, 31.3 mmol) and ethyl chloroformate (6 mL, 62.5 mmol). After 1 h at room temperature, the reaction mixture was diluted with EtOAc and washed successively with water, brine, dried (MgSO₄), filtered and concentrated under reduced pressure. The residue was purified by flash chromatography (hexane/EtOAc, 5/5) to give 4d (2.96 g, 76% yield) as a white solid.

Step e:

A solution of 4d (3.6 g, 11.5 mmol) in THF (100 mL) was stirred for 4 h under hydrogen (1 atm.) in the presence of 10% Pd/C (360 mg). The catalyst was removed by filtration through diatomaceous earth. The filtrate was concentrated under reduced pressure. To the resulting compound dissolved in THF (150 mL) was added Et₃N (4 mL, 28.9 mmol) followed by a toluene solution of phosgene (20%, 6.6 mL). After 45 min, water was added and the reaction mixture was extracted twice with EtOAc. The combined organic layers was washed with aqueous 1 N HCl and brine, dried (MgSO₄), filtered and concentrated under reduced pressure to give the cyclic urea (3.52 g, 99%) as a yellow solid. To a solution of the corresponding cyclic urea (2.9 g, 9.4 mmol) in THF (150 mL) and MeOH (50 mL) was added an aqueous 1 N LiOH solution (47 mL, 47 mmol). After 1 h, the reaction mixture was acidified using an aqueous HCl solution. The aqueous layer was extracted four times with EtOAc and the combined organic layers were washed with brine, dried (MgSO₄), filtered and concentrated under reduced pressure to give compound 4e (1.5 g, 98%) as a pink solid.

Step f:

A solution of DEAD (24 μL, 0.15 mmol) in THF (0.3 mL) was added dropwise to a solution of 4a (32 mg, 0.1 mmol), Ph₃P (39.5 mg, 0.15 mmol) and phenol 4e (24.7 mg, 0.15 mmol) in THF (1.5 mL) at room temperature. The reaction mixture was stirred at room temperature for 16 h then was concentrated under reduced pressure. The residue was purified by reverse phase HPLC (CombiPrep ADS-AQ 50×20 mm, 5μ, 120 Å, MeCN+0.10% TFA/water+0.10% TFA) to give the trifluoroacetic acid salt of compound 101 (6.3 mg, 11% yield) as a white solid.

Example 5

(Entry 118)

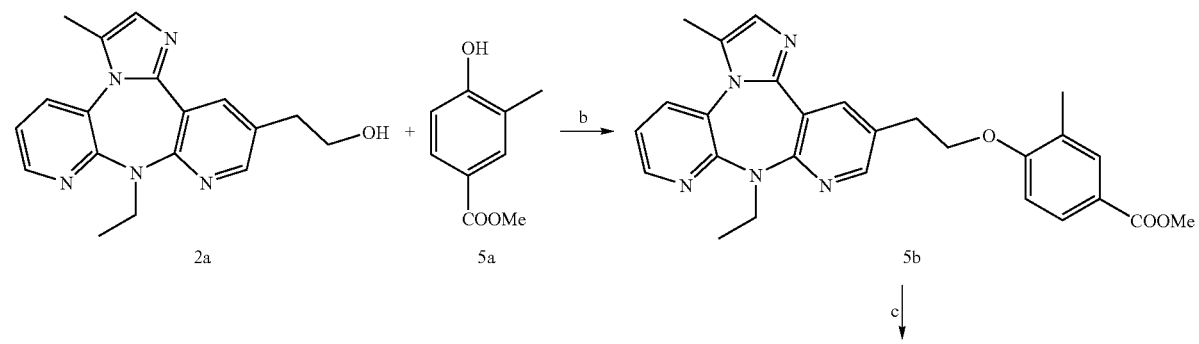

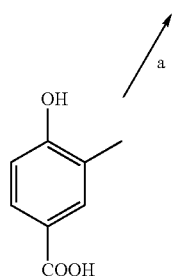

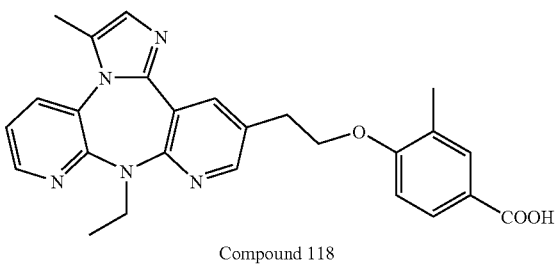

Compound 118

Step a:

To a solution of 4-hydroxy-3-methyl benzoic acid (5.13 g, 33.7 mmol) in MeOH (100 mL) was added concentrated HCl (1 mL). The reaction mixture was heated to reflux. After 16 h, the reaction mixture was concentrated under reduced pressure and the residue dissolved in EtOAc. The organic layer was washed with a saturated $NaHCO_3$ solution and brine, dried ($MgSO_4$) filtered and concentrated under reduced pressure. The solid was triturated with hexane/EtOAc (9/1) to give 5a (4.7 g, 84% yield) as a beige solid.

Step b:

A solution of DIAD (76.8 μL, 0.39 mmol) in THF (0.5 mL) was added dropwise to a solution of 2a (112.5 mg, 0.35 mmol), $Ph_3P$ (102.3 mg, 0.39 mmol) and phenol 5a (63.9 mg, 0.39 mmol) in THF (1.5 mL) at room temperature. The mixture was stirred for 1 h then was concentrated under reduced pressure. The residue was purified by flash chromatography ($CH_2Cl_2$/EtOAc; 1/1) to give compound 5b (99 mg, 60% yield) as a white solid.

Step c:

A solution of 5b (96 mg, 0.2 mmol) and aqueous 1 N NaOH solution (2 mL) in MeOH (0.5 mL) and THF (5 mL) was stirred at room temperature for 24 h. Aqueous 1 N HCl solution was added to the reaction mixture (pH~6) and the mixture was extracted with EtOAc twice. The combined organic phase were washed with water and brine, dried ($MgSO_4$) filtered and concentrated under reduced pressure. The resulting solid was triturated ($Et_2O$/hexane) filtered and dried to give compound 118 (41.8 mg, 45% yield) as a white solid.

Example 6

(Entry 112)

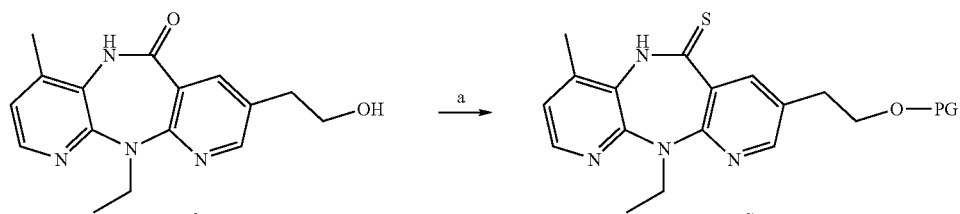

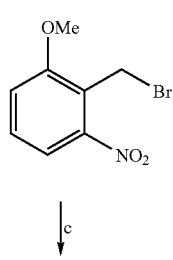

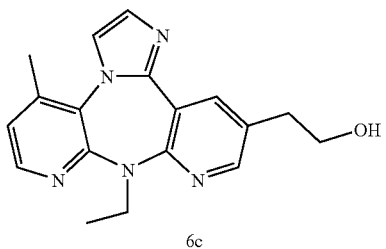

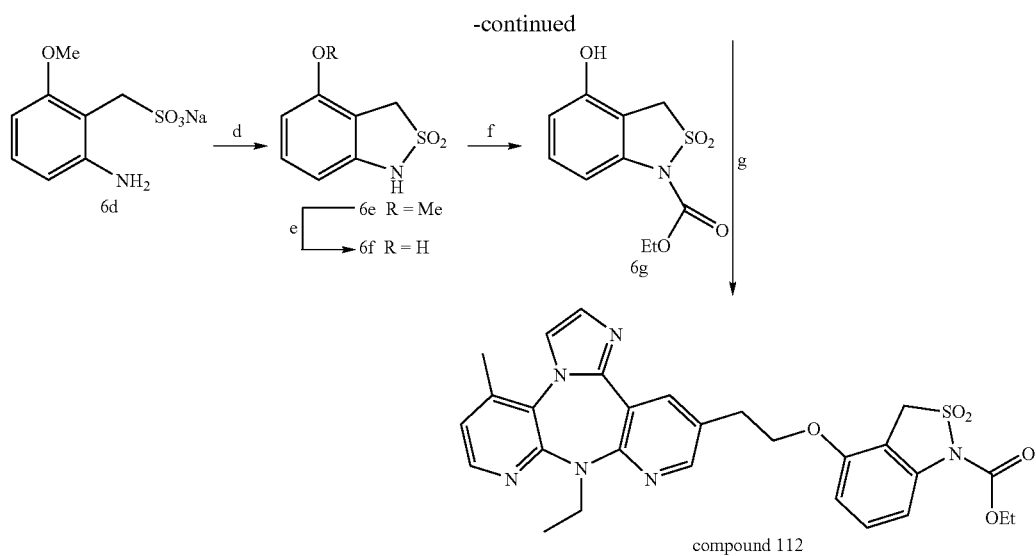

PG = tert-butyldimethylsilyl

Step a:

Following the procedure described for steps g and h in Example 1, 6a gave the desired protected intermediate 6b.

Step b:

Following the procedure described for step a in Example 3, 6b (643 mg, 1.5 mmol) gave compound 6c (348 mg, 72% yield) as a yellow solid.

Step c:

A solution of $Na_2SO_3$ (0.36 g, 3.36 mmol) in water (10 mL) was added to a solution of 2-(bromomethyl)-1-methoxy-3-nitrobenzene (Beckett, A. H.; Daisley, R. W.; Walker, J. *Tetrahedron* 1968, 24, 6093) (750 mg, 3.05 mmol) in acetone (5 mL). The solution was then stirred at reflux for 16 h, cooled to ambient temperature and concentrated under reduced pressure. The resulting paste was dissolved in hot ethanol and filtered while hot. The mother liquor was cooled in an ice bath and the solid that precipitated was collected via suction filtration and dried under reduced pressure to give a white solid (1.10 g) containing the desired product and NaBr. A portion of this solid (100 mg, 0.41 mmol) was dissolved in 50% EtOH in water (5 mL), 10% Pd/C (10 mg) was added and the resulting mixture was stirred under an atmosphere of hydrogen until the reaction was judged to be complete by HPLC (90 min). The mixture was diluted with water (5 mL), filtered and concentrated to give 6d (86 mg, 97% yield).

Step d:

A solution of 6d (35 mg, 0.16 mmol) in $POCl_3$ (3.0 mL) was heated to reflux for 2 h. The reaction was cooled to room temperature and concentrated under reduced pressure. A mixture of ice and water was added carefully and the solution was rendered basic with aqueous 2 N NaOH solution. The mixture was heated to 70° C. for 10 min and filtered while hot. The filtrate was acidified with aqueous concentrated HCl solution while cooled in an ice bath. The product which precipitated was collected via suction filtration to give 6e (19 mg, 60%).

Step e:

A solution of 6e (0.8 g, 4.0 mmol) in $CH_2Cl_2$ (15 mL) was cooled to −78° C. A 3.3 M solution of $BBr_3$ in $CH_2Cl_2$ (7.9 mL, 32.3 mmol) was then added slowly over 15 min. After the addition was complete, the reaction mixture was allowed to warm to room temperature over 4 h, then cautiously poured onto a mixture of ice and water. The mixture was extracted with EtOAc. The combined organic phases were washed with water and brine, dried ($MgSO_4$), filtered and concentrated under reduced pressure. The resulting solid was purified by flash chromatography (hexane/EtOAc, 1/1) to give 6f (0.55 g, 74%).

Step f:

Ethyl chloroformate (2.71 mL, 28.3 mmol) was added over 10 min to an ice-cold solution of 6f (1.75 g, 9.45 mmol) and $Et_3N$ (5.27 mL, 37.8 mmol) in THF (60 mL). The resulting suspension was stirred at ambient temperature for 2 h. Water was then added and the mixture was extracted with EtOAc. The organic layer was washed with aqueous 1.0 N HCl solution, aqueous saturated $NaHCO_3$ solution and brine, dried ($MgSO_4$) filtered and concentrated under reduced pressure to give a beige solid (2.54 g, 86%). To this solid (2.52 g, 8.04 mmol) in 25% EtOH in THF (80 mL) was added $NH_4OH$ (23 mL of 28% solution, 150 mmol) and the resulting solution was stirred for 90 min. The mixture was concentrated under reduced pressure and the residue was purified by flash chromatography (hexane/EtOAc, 7/3) to give 6 g (1.41 g, 68%).

Step g:

A solution of DIAD (200 μL, 1.0 mmol) in THF (0.7 mL) was added over 2 h to an ice-cold solution of 6c (217 mg, 0.68 mmol), 6 g (260 mg, 1.0 mmol) and $PPh_3$ (265 mg, 1.0 mmol) in THF (6.7 mL). The reaction mixture was stirred at 25° C. for 16 h then was concentrated under reduced pressure. The residue was purified by flash chromatography (EtOAc/$CH_2Cl_2$, 3/1) to give compound 112 (320 mg, 86% yield) as a white powder.

Example 7

(Entries 113, 114, 115)

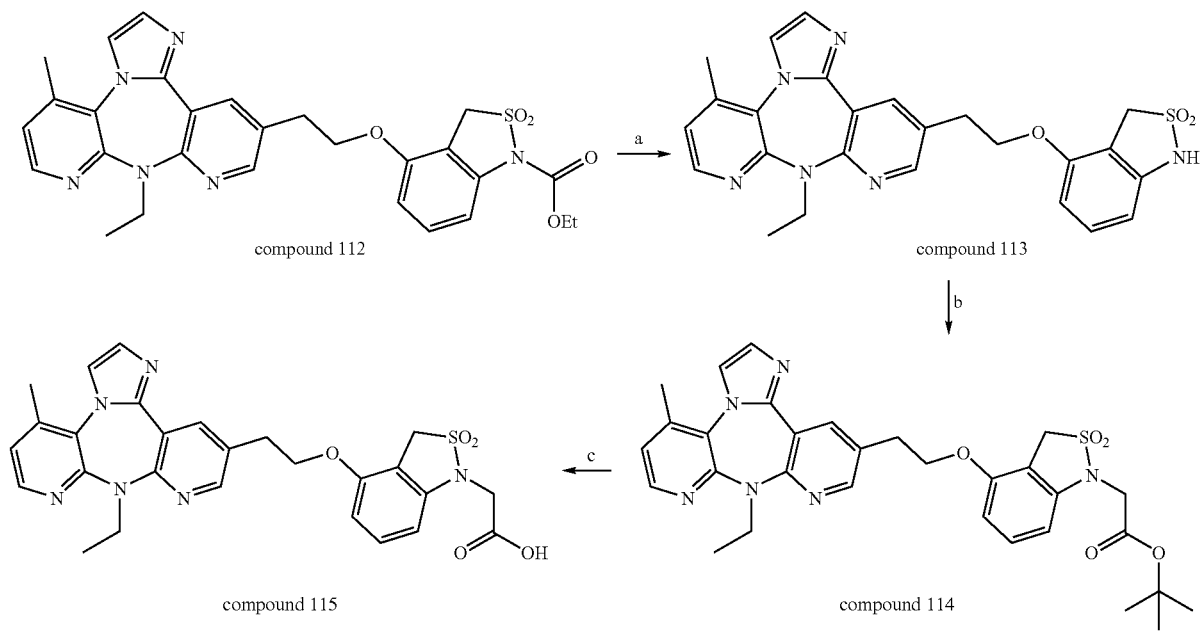

Step a:

A solution of compound 112 (295 mg, 0.52 mmol) and ammonium hydroxide (0.8 mL) in THF (45 mL) and EtOH (15 mL) was stirred at room temperature for 16 h. The reaction mixture was concentrated under reduced pressure. The mixture was diluted with EtOAc and the resulting solution was washed successively with aqueous1 N HCl solution, water and brine, dried (MgSO$_4$), filtered and evaporated to dryness. The resulting solid was triturated with an ether/hexane solution (1/1) to give compound 113 (140 mg, 55% yield) as a beige solid.

Step b:

To a solution of compound 113 (71.5 mg, 0.12 mmol) in DMF (10 mL) was added K$_2$CO$_3$ followed by tert-butyl 2-bromoacetate (72.5 µL, 0.45 mmol). After 1 h, the reaction mixture was diluted with EtOAc and was washed successively with water, brine, dried (MgSO$_4$), filtered, and evaporated to dryness. The resulting residue was purified by flash chromatography (hexane/EtOAc, 1/3) to give compound 114 (77.2 mg, 72% yield) as a white powder.

Step c:

A solution of compound 114 (71.5 mg, 0.12 mmol) and TFA (2 mL) in CH$_2$Cl$_2$ (2 mL) was stirred at room temperature overnight. The reaction mixture was evaporated to dryness and a mixture of hexane/EtOAc was added to give a precipitate. The resulting solid was filtered, rinsed with EtOAc and dried to give compound 115 (58 mg, 90% yield) as a white solid.

Example 8

(Entry 105)

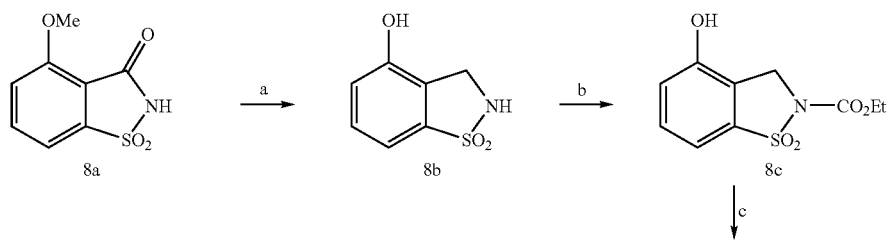

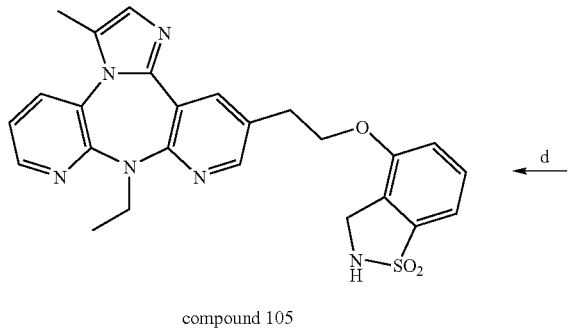

compound 105

-continued

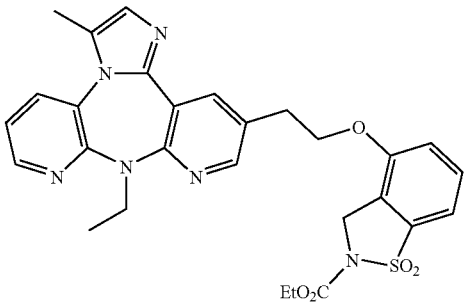

8d

Step a:

A 1.0 M LiAlH$_4$ solution in THF (5.8 mL, 5.8 mmol) was added to a solution of 8a (Hlasta, D. J.; Court, J. J.; Dessai, C.; *Tetrahedron Lett.* 1991, 32, 7179) (250 mg, 1.1 mmol) in THF (10 mL). The resulting solution was stirred at ambient temperature for 16 h. The reaction mixture was carefully quenched with a saturated solution of Rochelle's salt, diluted with EtOAc and stirred vigorously for 20 min. The mixture was filtered through diatomaceous earth and the filtrate was concentrated under reduced pressure give a white solid (162 mg, 70% yield). This solid (130 mg, 0.65 mmol) was dissolved in CH$_2$Cl$_2$ (10 mL) and the solution was cooled to −78° C. A 3.5 M BBr$_3$ solution in CH$_2$Cl$_2$ (2.0 mL, 7 mmol) was added, the cold bath was removed and the resulting mixture was aged for 16 h. The reaction was quenched by careful addition of water and the mixture was extracted with EtOAc. The combined organic layers were dried (MgSO$_4$), filtered and concentrated under reduced pressure. The residue was purified by flash chromatography (70 to 80% EtOAc in hexane) to give 8b (96 mg, 79% yield).

Step b:

To sultam 8b (92 mg, 0.5 mmol) dissolved in pyridine (4 mL) was added ethyl chloroformate (100 μL, 1.1 mmol). The reaction was stirred for 16 h at room temperature then was concentrated under reduced pressure. The mixture was extracted with EtOAc. The combined organic layers were washed successively with aqueous 1.0 N HCl solution, water, saturated NaHCO$_3$ solution and brine, dried (MgSO$_4$), filtered and concentrated under reduced pressure to give the carbonate/carbamate derivative. This material was dissolved in 10% EtOH in EtOAc (2 mL), a 2.0 M solution of NH$_3$ in EtOH (0.6 mL, 1.2 mmol) was added and the solution stirred for 1 h at ambient temperature. The reaction mixture was concentrated and purified by flash chromatography (hexane/EtOAc 1/1) to give 8c (42 mg, 32% yield).

Step c:

Following the procedure described for step c in Example 2, 8c gave compound 8d (95 mg, 75% yield).

Step d:

To a solution of 8d (95 mg, 0.17 mmol) in EtOH/THF (6/2 mL) was added ammonium hydroxide (4 mL). After stirring for 16 h, the reaction mixture was acidified using aqueous 4 N HCl solution and was extracted with EtOAc. The organic layer was dried (MgSO$_4$), filtered and concentrated under reduced pressure to give compound 105 (64.2 mg, 77% yield) as a white solid.

Example 9

(Entry 107)

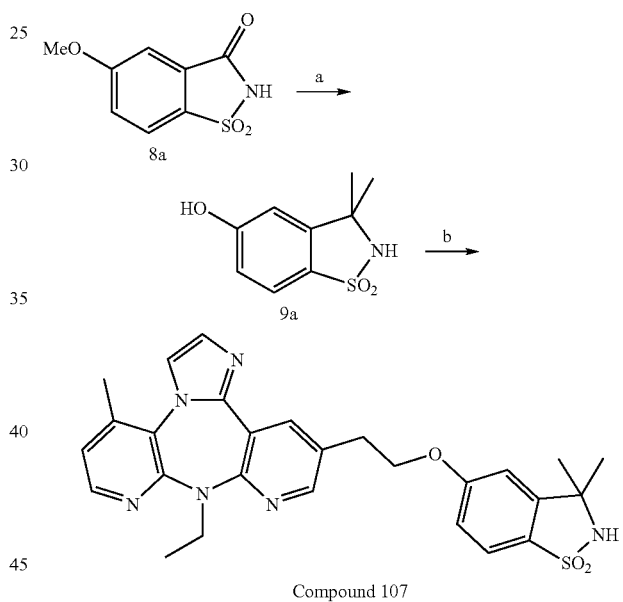

Compound 107

Step a

Saccharine 8a (290 mg, 4.08 mmol) was dissolved in xylenes (10 mL) containing a small amount of activated charcoal (50 mg). DMF (2 drops) and freshly distilled SOCl$_2$ (0.30 mL, 4.08 mmol) were added and the resulting mixture was heated to reflux for 15 h. The cooled reaction mixture was concentrated under reduced pressure to give a paste. The paste was dissolved in THF and the resulting solution was then added dropwise to a solution of MeMgCl (1.36 mL of a 3.0 M solution in THF, 4.08 mmol) in THF (7 mL). The resulting solution was stirred at 40° C. for 24 h. The reaction mixture was concentrated under reduced pressure and the residue was purified by flash chromatography (40 to 60% EtOAc in hexane) to give the desired compound (9a methyl ether, 124 mg, 40%). To a solution of this material (100 mg, 0.44 mmol) in CH$_2$Cl$_2$ (50 mL) at −78° C. was added a 1.0 M solution of BBr$_3$ (2.64 mL, 2.64 mmol) in CH$_2$Cl$_2$. The resulting mixture was stirred for 16 h at ambient temperature. After careful addition of water, the mixture was extracted with EtOAc. The combined organic extracts were washed with water and brine, dried (MgSO$_4$) filtered and evaporated to dryness. The residue was purified flash chromatography (hexane/EtOAc 6/4) to give compound 9a (54 mg, 58% yield)

Step b:

To a solution of sultam 9a (64 mg, 0.3 mmol), PPh$_3$ (78 mg, 0.3 mmol) and compound 6c (64.3 mg, 0.2 mmol) in THF (2 mL) was slowly added DEAD (0.059 mL, 0.3 mmol) in THF (0.5 mL). The reaction was stirred at room temperature overnight then was concentrated under reduced pressure. The residue was purified by flash chromatography (EtOAc/CH$_2$Cl$_2$, 2/1) to give compound 107 (47.2 mg, 46% yield) as a white solid.

Example 10

(Entry 102)

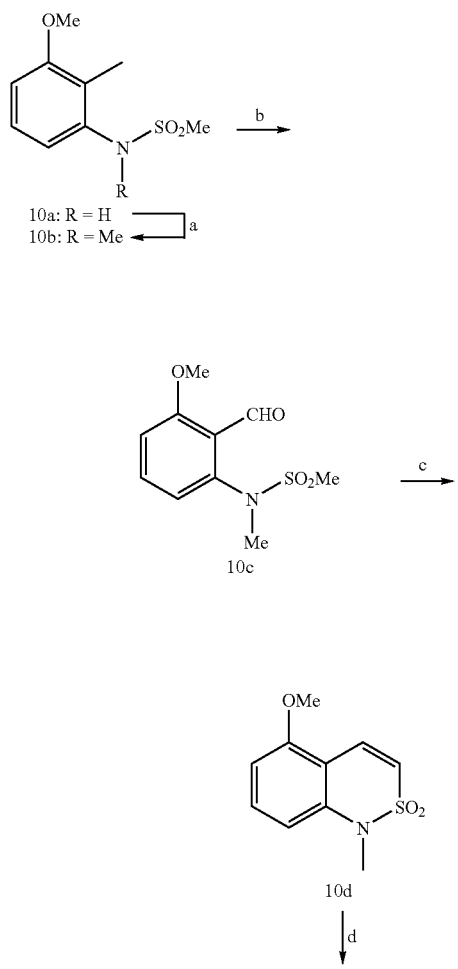

-continued

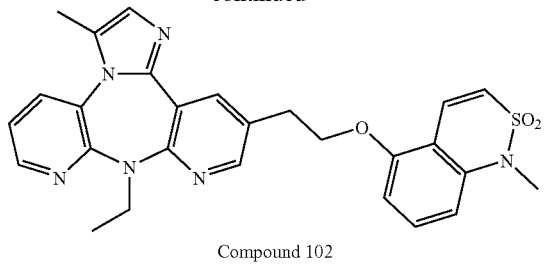

Compound 102

Step a:

A slurry of N-(3-methoxy-2-methylphenyl)methane-sulfonamide 10a (Blondet, D.; Pascal, J.-C. *Tetrahedron Lett.* 1994, 35, 2911) (4.5 g, 20.9 mmol), K$_2$CO$_3$ (4.33 g, 31.4 mmol) and MeI (6.5 mL, 105 mmol) in DMF (100 mL) was stirred vigorously for 5 days. The reaction mixture was poured into water (250 mL). The mixture was stirred for 10 min and was extracted with ether. The combined organic extracts were washed with water and brine, dried (MgSO$_4$), filtered and concentrated under reduced pressure to give 10b (5.10 g).

Step b:

A solution of 10b (1.0 g, 4.37 mmol) in MeCN (15 mL) was added to a solution of K$_2$S$_2$O$_8$ (2.35 g, 8.73 mmol) and CuSO$_4$ (219 mg, 0.87 mmol) in water (15 mL). Pyridine (0.71 mL, 8.73 mmol) was introduced and the resulting mixture was stirred vigorously at reflux for 2 h. After cooling to room temperature, the suspension was filtered. The filtrate was extracted with EtOAc and the combined extracts were washed with aqueous 1.0 N NaOH solution, aqueous 1.0 N HCl solution, water and brine, dried (MgSO$_4$) filtered and concentrated under reduced pressure. The resulting syrup (731 mg) was dissolved in CH$_2$Cl$_2$ (15 mL) containing water (two drops). Dess-Martin periodinane (1.69 g, 3.83 mmol) was added and the resulting solution was stirred for 90 min. A mixture of equal parts of aqueous 10% Na$_2$S$_2$O$_3$ solution and aqueous saturated NaHCO$_3$ solution was added and the resulting two-phase mixture was stirred until both layers were clear. The mixture was extracted with EtOAc and the combined organic extracts were washed successively with aqueous saturated NaHCO$_3$ solution, water and brine, dried (MgSO$_4$), filtered and concentrated under reduced pressure. The residue was purified by flash chromatography (hexane/EtOAc, 40 to 70%) to give compound 10c (432 mg, 41% yield).

Step c:

KOtBu (1.92 g, 17.1 mmol) was added in two portions over 10 min to a solution of aldehyde 10c (3.80 g, 15.6 mmol) in THF (300 mL). The reaction was allowed to stir for 10 min at ambient temperature then was quenched by the addition of water. The mixture was extracted with CH$_2$Cl$_2$. The combined organic layers were washed with water and brine, dried (MgSO$_4$), filtered and concentrated under reduced pressure. The residue was purified by flash chromatography (hexane/EtOAc, 2/8) to give the desired intermediate (2.97 g, 85%). A 1.0 M BBr$_3$ solution in CH$_2$Cl$_2$ (3.95 mL, 3.95 mmol) was added to an ice-cold solution of this material (120 mg, 0.49 mmol) in CH$_2$Cl$_2$ (15 mL). The cold bath was then removed and the resulting solution was stirred for 16 h at ambient temperature. Water was carefully added to the reaction mixture and the mixture was extracted with EtOAc. The combined extracts were washed with water and brine, dried (MgSO$_4$), filtered and concentrated under reduced pressure. The residue was purified by flash chromatography (EtOAc in hexane, 30 to 100%) to give 10d (76 mg, 73%).

Step d:

Following the procedure described for step c in Example 2, phenol 10d gave compound 102 (80 mg, 65% yield).

Example 11

(Entry 103)

Step b:

A solution of 11b (997 mg, 3.85 mmol) and ammonium hydroxide (9 mL) in THF (19 mL) was stirred at room temperature for 4 h. The reaction mixture was evaporated to dryness. The residue was purified by flash chromatography (hexane/EtOAC, 40/60, containing MeOH 1%) to give 11c as a white solid (595 mg, 95% yield).

Step c:

To an ice-cold solution of 11c (291 mg, 1.78 mmol) in CH$_2$Cl$_2$ (20 mL) was added a 1.0 M BBr$_3$ solution in CH$_2$Cl$_2$ (3.6 mL, 3.6 mmol). The cold bath was then removed and the resulting solution was stirred for 16 h at ambient

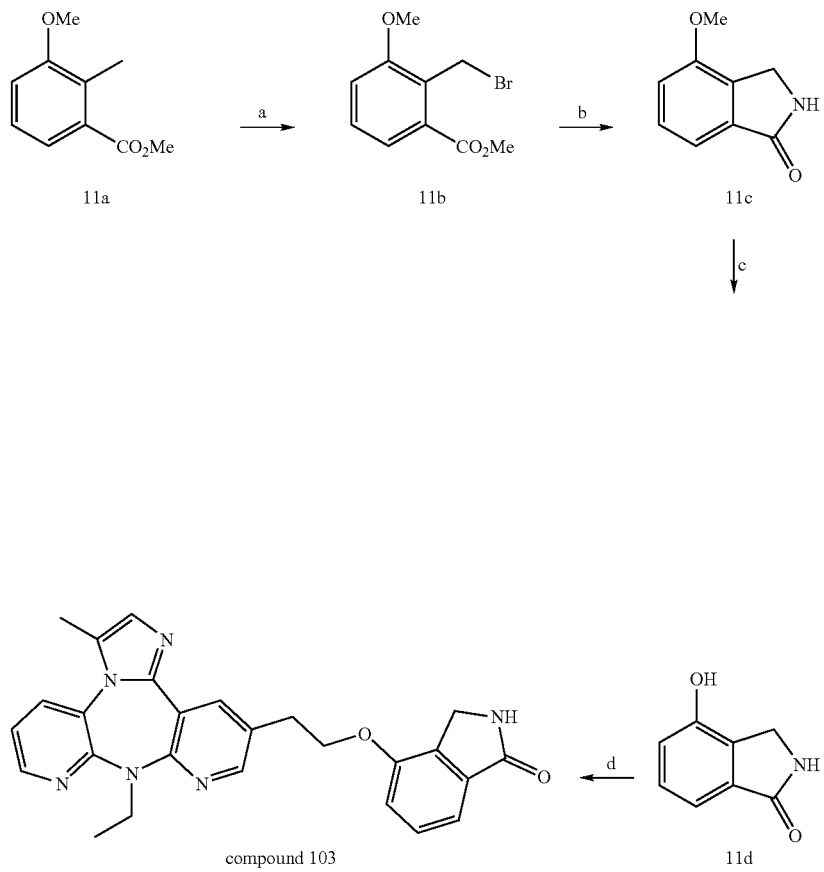

Step a:

A solution of 11a (2.58 g, 14.3 mmol), NBS (2.79 g, 15.7 mmol) and AIBN (232 mg, 1.4 mmol) in CCl$_4$ (20 mL) was refluxed for 3 h. The reaction mixture was cooled to room temperature and the resulting suspension was filtered. The filtrate was concentrated under reduced pressure and the residue was purified by flash chromatography (hexane/CH$_2$Cl$_2$, 75/25) to give 11b (3.4 g, 92% yield) as a white solid.

temperature. The reaction was carefully quenched by the addition of water and the mixture was extracted with EtOAc. The combined extracts were washed with water and brine, dried (MgSO$_4$), filtered and evaporated to dryness to give 11d (232 mg, 87% yield) as beige solid.

Step d:

Following the procedure described for step c in Example 2, phenol 11 d gave compound 103 (30.4 mg, 65% yield).

TABLE 1

| Entry # | R¹ | R² | R³ | R⁴ | W | MS ES⁺ (MH) |
|---|---|---|---|---|---|---|
| 101 | H | H | H | Me | 5-(3,4-dihydroquinazolin-2(1H)-one-5-yl) | 468 |
| 102 | H | H | Me | H | 1-methyl-1H-benzo[c][1,2]thiazine 2,2-dioxide | 515 |
| 103 | H | H | Me | H | isoindolin-1-one-4-yl | 453 |
| 104 | H | H | Me | H | 3,4-dihydro-2H-benzo[e][1,2]thiazine 2,2-dioxide | 503 |
| 105 | H | H | Me | H | 2,3-dihydrobenzo[d]isothiazole 1,1-dioxide | 489 |
| 106 | H | H | Me | H | 4H-benzo[d][1,3]oxazin-2(1H)-one | 469 |
| 107 | H | Me | H | H | 3,3-dimethyl-2,3-dihydrobenzo[d]isothiazole 1,1-dioxide | 517 |
| 108 | H | Me | H | H | 3,4-dihydroquinazolin-2(1H)-one | 468 |
| 109 | H | H | H | H | 3,4-dihydroquinazolin-2(1H)-one | 454 |
| 110 | H | H | Me | H | 3,4-dihydroisoquinolin-1(2H)-one | 467 |
| 111 | H | H | Me | H | 1,3-dimethyl-3,4-dihydroquinazolin-2(1H)-one | 496 |
| 112 | H | Me | H | H | ethyl 2,2-dioxido-1,3-dihydrobenzo[c]isothiazole-1-carboxylate | 561 |
| 113 | H | Me | H | H | 1,3-dihydrobenzo[c]isothiazole 2,2-dioxide | 489 |

TABLE 1-continued
| Entry # | R¹ | R² | R³ | R⁴ | W | MS ES⁺ (MH) |
|---|---|---|---|---|---|---|
| 114 | H | Me | H | H | 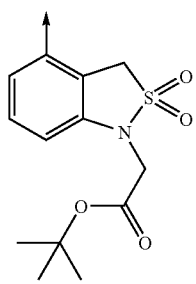 | 603 |
| 115 | H | Me | H | H | 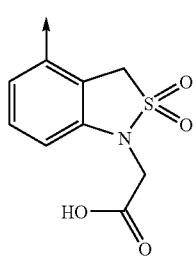 | 547 |
| 116 | H | H | Me | H | 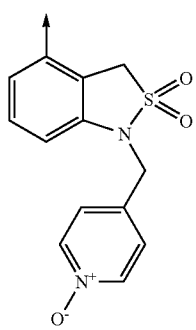 | 415 |
| 117 | H | H | H | H | 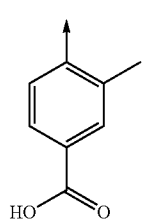 | 442 |
| 118 | H | H | Me | H | (see structure) | 456 |
| 119 | H | H | H | H | 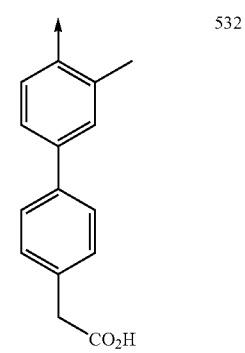 | 532 |
| 120 | H | H | Me | H | 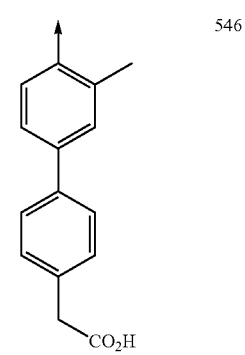 | 546 |
| 121 | H | H | Me | H | 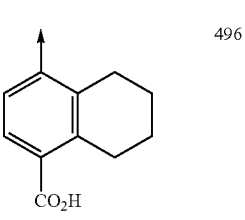 | 496 |

TABLE 1-continued

| Entry # | R¹ | R² | R³ | R⁴ | W | MS ES⁺ (MH) |
|---|---|---|---|---|---|---|
| 122 | H | H | Me | H | (4-carboxy-1-naphthyl) | 492 |

REVERSE TRANSCRIPTASE (RT) AND CELL-BASED ASSAYS

The assays are as described in WO 01/96338A1, the contents of which are hereby incorporated herein. The results are listed in Table 2 as $IC_{50}$(nM) and $EC_{50}$ (nM).

Table legend:
$IC_{50}$ (nM) A=>100; B=100-50; C=<50
$EC_{50}$ (nM) A>50; B=10-50; C<10; NT=not tested

TABLE 2

| Entry # | $IC_{50}$ WT | $IC_{50}$ K103N/Y181C | $EC_{50}$ WT |
|---|---|---|---|
| 101 | C | A | NT |
| 102 | C | C | C |
| 103 | C | A | C |
| 104 | C | B | NT |
| 105 | C | C | NT |
| 106 | C | A | NT |
| 107 | C | C | NT |
| 108 | C | C | NT |
| 109 | C | C | NT |
| 110 | C | A | NT |
| 111 | C | A | NT |
| 112 | C | C | NT |
| 113 | C | B | NT |
| 114 | C | B | NT |
| 115 | C | B | A |
| 116 | C | C | NT |
| 117 | C | A | C |
| 118 | C | C | NT |
| 119 | C | C | C |
| 120 | C | B | NT |
| 121 | C | A | NT |
| 122 | C | A | NT |
| 123 | C | A | NT |
| 124 | C | B | C |
| 125 | C | A | C |
| 126 | B | A | NT |
| 127 | C | A | NT |

The invention claimed is:

1. A compound represented by formula 1:

(1)

wherein

R¹ is selected from the group consisting of H, halogen, $(C_{1-4})$alkyl, $O(C_{1-4})$alkyl, and haloalkyl;

R² is H or Me;

R³ is H or $(C_{1-4})$alkyl;

R⁴ is H or $(C_{1-4})$alkyl;

R⁵ is $(C_{1-4})$alkyl, $(C_{1-4})$alkyl$(C_{3-7})$cycloalkyl, or $(C_{3-7})$cycloalkyl; and W is selected from:

wherein, a) one of Y is $SO_2$ and the other Y is NR⁶, provided that both are not the same, wherein R⁶ is selected from the group consisting of: H, $C(O)O(C_{1-4}$alkyl, $(C_{1-4})$alkyl or $(C_{1-4})$ alkyl substituted with either a pyridinyl-N-oxide or $C(O)OR^8$ wherein R⁸ is H or $(C_{1-4})$ alkyl; and each R⁹ is independently H or $(C_{1-4})$ alkyl; and b) E is $CR^{10}R^{10}$ wherein each R¹⁰ is independently H or $(C_{1-4})$ alkyl, J is $CH_2$ and the dotted line represents a single bond; or c) E and J are both CR¹¹ wherein R¹¹ is H or $(C_{1-4})$ alkyl and the dotted line represents a double bond; or W is selected from:

wherein, m is 1 or 2,

R¹² is H or $C_{(1-4)}$ alkyl,

R¹³ is H or $(C_{1-4})$ alkyl, and

Z is O or Z is $NR_{14}$ wherein R¹⁴ is H or $(C_{1-4})$ alkyl; or

W is selected from a group of aromatic radicals consisting of:

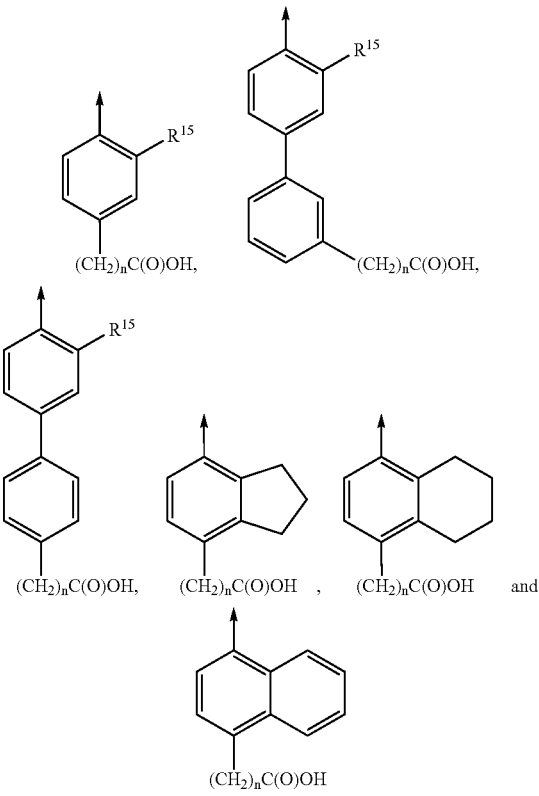

wherein $R^{15}$ is $(C_{1-4})$ alkyl or $CF_3$, and n is the integer 0, 1 or 2, or a pharmaceutically acceptable salt or ester thereof.

2. The compound according to claim 1, wherein $R^1$ is selected from the group consisting of: H, Cl, F, $(C_{1-4})$ alkyl and $CF_3$; $R^2$, $R^3$ and $R^4$ is each independently H or Me; $R^5$ is ethyl or cyclopropyl;

W is:

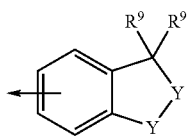

wherein Y is $SO_2$ and the other Y is $NR^6$, provided that both are not the same, $R^6$ is H, C(O)OMe, C(O)OEt, (4-pyridinyl-N-oxide)methyl, $CH_2C(O)OH$, $CH_2C(O)OMe$, $CH_2C(O)OEt$ or $CH_2C(O)OCMe_3$, and each $R^9$ is independently H or Me; or

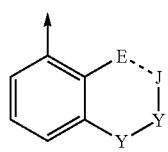

wherein E is $CR^{10}R^{10}$ wherein each of $R^{10}$ is independently H or Me, J is $CH_2$ and the dotted line represents a single bond; or both E and J are $CR^{11}$ wherein $R^{11}$ is H or Me and the dotted line represents a double bond; one of Y is $SO_2$ and the other Y is $NR^6$ wherein $R^6$ is hydrogen or methyl; or

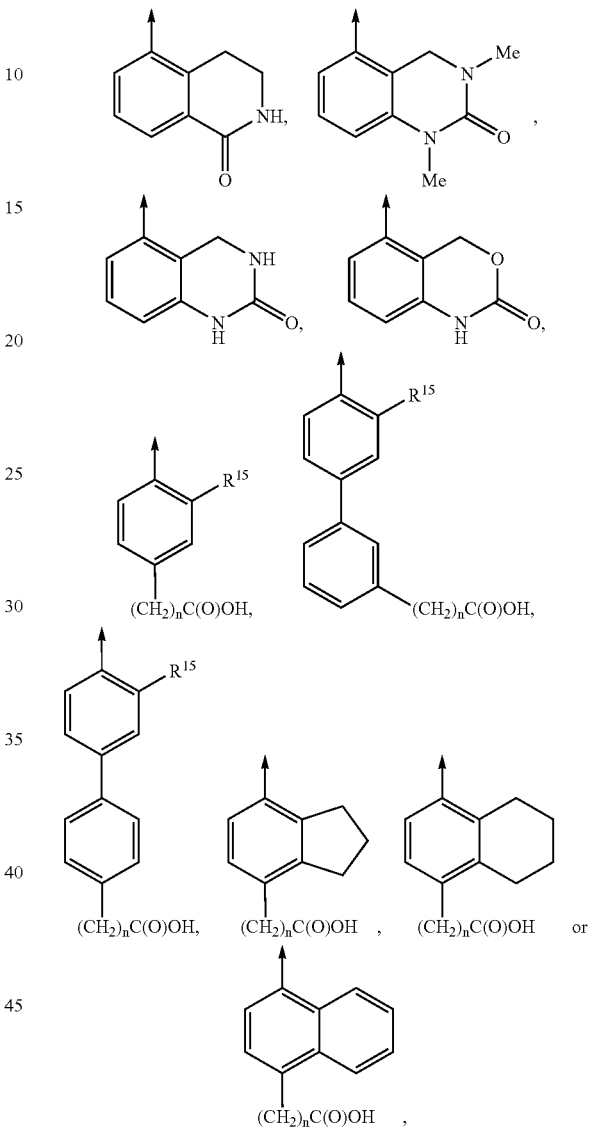

wherein $R^{15}$ is Me or Et, and n is 0 or 1.

3. The compound according to claim 2, wherein $R^{15}$ is Me.

4. The compound according to claim 3, wherein $R^1$ is H, Cl, F and Me; $R^2$ is H or Me;

W is:

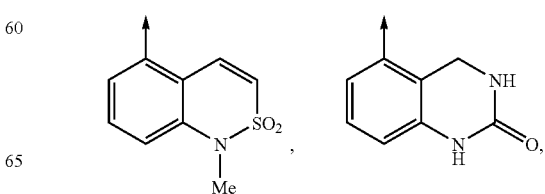

-continued

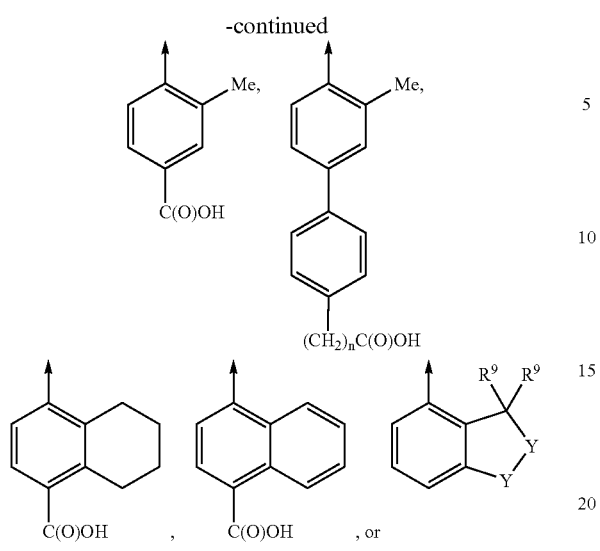

wherein Y is SO₂ and the other Y is NR⁶, provided that both are not the same, R⁶ is H, C(O)OEt, (4-pyridinyl-N-oxide) methyl, CH₂C(O)OH, CH₂C(O)OMe, CH₂C(O)OEt or CH₂C(O)OCMe₃, and each R⁹ is independently H or Me.

5. The compound according to claim 4, wherein R³ is Me, R⁶ is H, C(O)OEt or (4-pyridinyl-N-oxide)methyl, and W is:

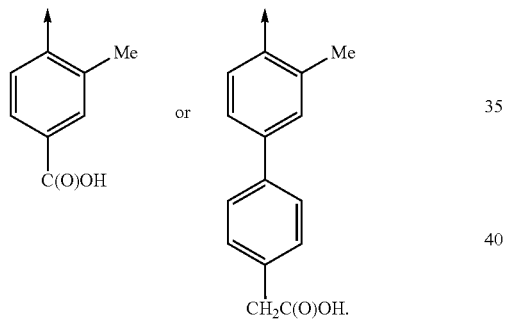

6. The compound according to claim 3, wherein W is:

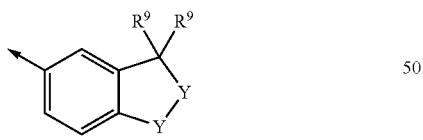

wherein one Y is SO₂ and the other Y is NR⁶, provided that both are not the same, R⁶ is H, C(O)OEt, CH₂C(O)OH, CH₂C(O)OCMe₃, (4-pyridinyl-N-oxide)methyl; and each R⁹ is independently H or Me.

7. The compound according to claim 6, wherein R⁶ is H and each R⁹ is Me.

8. A pharmaceutical composition for the treatment of HIV infection, comprising a compound of formula 1 according to claim 1, or a pharmaceutically acceptable salt or ester thereof, in combination with a pharmaceutically acceptable carrier.

9. A method for the treatment of HIV infection, comprising administering to a patient an HIV inhibiting amount of a compound of formula 1 according to claim 1, or a pharmaceutically acceptable salt or ester thereof.

10. A method for the treatment of HIV infection, comprising administering to a patient an HIV inhibiting amount of a pharmaceutical composition according to claim 8.

11. A process for producing a compound of formula 1 according to claim 1, comprising the step:

coupling a compound of formula 2:

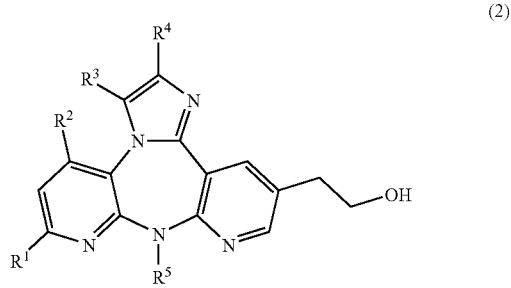

(2)

wherein R¹, R², R³, R⁴, and R⁵ are as defined in claim 1, with a phenolic derivative selected from:

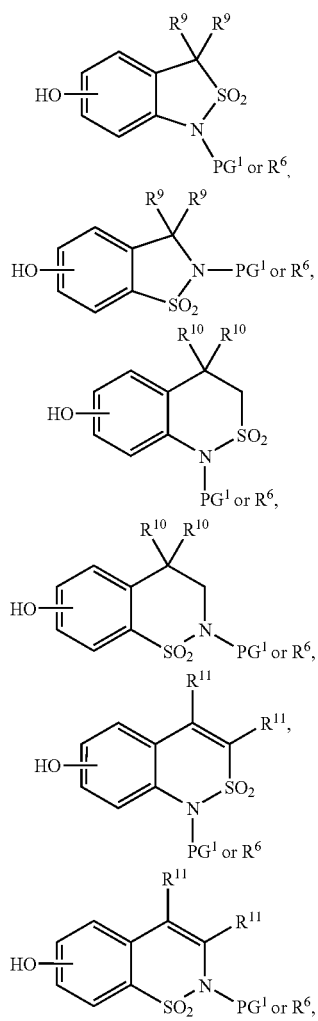

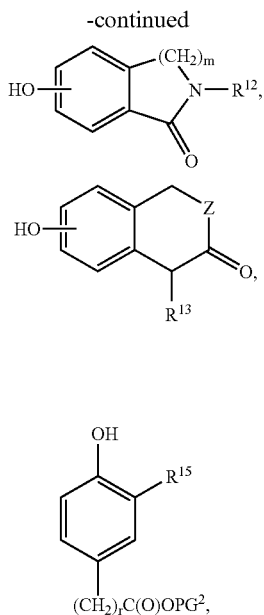

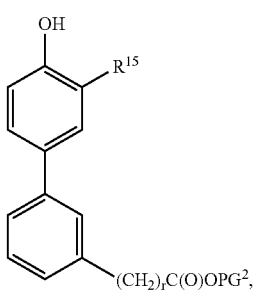

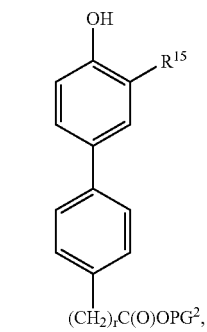

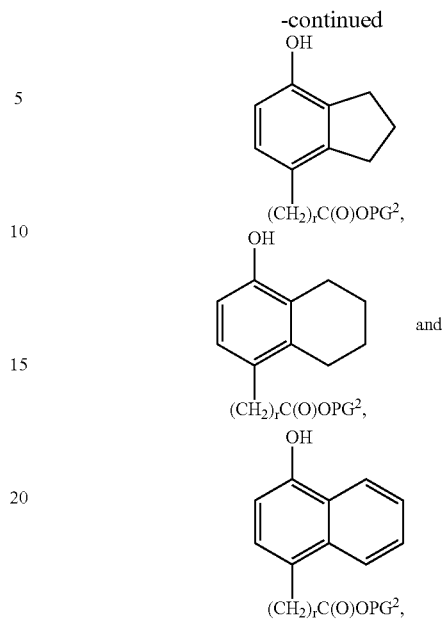

wherein PG$^1$ is a nitrogen protecting group and PG$^2$ is a carboxy protecting group, said protecting groups being removable under mildly acidic, mildly alkaline or reductive conditions, and R$^6$, R$^9$, R$^{10}$, R$^{11}$, R$^{12}$, R$^{13}$, R$^{14}$, R$^{15}$, m, n, and Z are as defined in claim 1.

12. The process according to claim 11, wherein said carboxy protecting group is selected from: alkyl esters; aralkyl esters; and esters that can be cleaved by mild base treatment or mild reductive means.

13. The process according to claim 11, wherein said nitrogen protecting group is selected from: Boc (tert-butyloxycarbonyl) and alkyl carbamates.

14. An intermediate compound of formula 2:

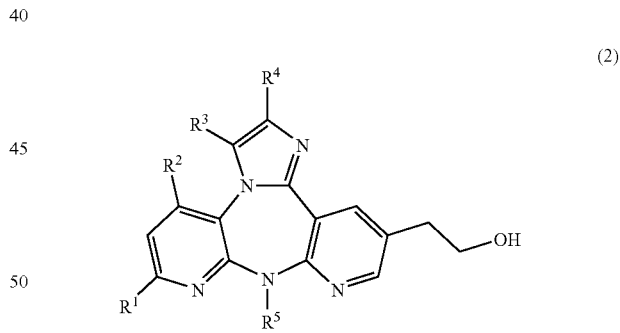

(2)

wherein R$^1$, R$^2$, R$^3$, R$^4$, and R$^5$ are as defined in claim 1.

* * * * *